(12) United States Patent
Cooymans et al.

(10) Patent No.: US 8,846,672 B2
(45) Date of Patent: Sep. 30, 2014

(54) IMIDAZOPYRIDINES AS RESPIRATORY SYNCYTIAL VIRUS ANTIVIRAL AGENTS

(75) Inventors: Ludwig Paul Cooymans, Beerse (BE); Lili Hu, Mechelen (BE); Tim Hugo Maria Jonckers, Edegem (BE); Pierre Jean-Marie Bernard Raboisson, Rosieres (BE); Abdellah Tahri, Anderlecht (BE); Steven Maurice Paula Van Hoof, Merelbeke (BE); Sandrine Marie Helene Vendeville, Woluwe-Saint-Pierre (BE)

(73) Assignee: Janssen R&D Ireland (IE)

( * ) Notice: Subject to any disclaimer, the term of this patent is extended or adjusted under 35 U.S.C. 154(b) by 0 days.

(21) Appl. No.: 13/993,692

(22) PCT Filed: Dec. 16, 2011

(86) PCT No.: PCT/EP2011/073017
§ 371 (c)(1),
(2), (4) Date: Jun. 13, 2013

(87) PCT Pub. No.: WO2012/080451
PCT Pub. Date: Jun. 21, 2012

(65) Prior Publication Data
US 2013/0324527 A1    Dec. 5, 2013

(30) Foreign Application Priority Data
Dec. 16, 2010    (EP) ..................... 10195474

(51) Int. Cl.
| | | |
|---|---|---|
| *A61K 31/5377* | (2006.01) | |
| *A61K 31/496* | (2006.01) | |
| *A61K 31/495* | (2006.01) | |
| *A61K 31/4427* | (2006.01) | |
| *C07D 413/14* | (2006.01) | |
| *C07D 417/04* | (2006.01) | |
| *C07D 487/04* | (2006.01) | |
| *C07D 471/04* | (2006.01) | |

(52) U.S. Cl.
CPC ............ *C07D 487/04* (2013.01); *C07D 471/04* (2013.01)
USPC ........ 514/233.2; 514/249; 514/300; 514/303; 544/117; 544/350; 546/118; 546/121

(58) Field of Classification Search
USPC .................. 514/233, 249, 300; 544/117, 350; 546/118, 121
See application file for complete search history.

(56) References Cited

U.S. PATENT DOCUMENTS

| 6,489,338 B2 | 12/2002 | Yu et al. |
| 6,506,738 B1 | 1/2003 | Yu et al. |
| 6,534,535 B1 | 3/2003 | Zhu et al. |
| 6,919,331 B2 | 7/2005 | Yu et al. |
| 7,361,657 B2 | 4/2008 | Janssens et al. |
| 7,528,149 B2 | 5/2009 | Janssens et al. |
| 2002/0016309 A1 | 2/2002 | Yu et al. |
| 2004/0166137 A1 | 8/2004 | Lackey |
| 2013/0261151 A1 | 10/2013 | Cooymans et al. |
| 2013/0267508 A1 | 10/2013 | Cooymans et al. |
| 2013/0267555 A1 | 10/2013 | Cooymans et al. |
| 2013/0267556 A1 | 10/2013 | Cooymans et al. |
| 2013/0324527 A1 | 12/2013 | Cooymans et al. |

FOREIGN PATENT DOCUMENTS

| WO | WO 98/01428 | 1/1998 |
| WO | WO 00/20400 | 4/2000 |
| WO | WO 01/95910 | 12/2001 |
| WO | WO 02/26228 | 4/2002 |
| WO | WO 03/053344 | 4/2003 |

OTHER PUBLICATIONS

Ito, Nobuyuki. Cancer Science 94(1), (2003) 3-8.*
Database Registry Chemical Abstracts Service, Columbus, Ohio, Accession No. RN 941045-14-3 and RN 931665-23-5. Entered STN: Jul. 4, 2007 and Apr. 22, 2007.*
International Search Report—PCT/EP2011/073008, dated, Mar. 28, 2012.
International Search Report—PCT/EP2011/073011, dated, Mar. 27, 2012.
International Search Report—PCT/EP2011/073014, dated Mar. 28, 2012.
International Search Report—PCT/EP2011/073016, dated Mar. 27, 2012.
International Search Report—PCT/EP2011/073017, dated Mar. 28, 2012.
Banker, et al., Modern Pharmaceutics, 3 edition, 1996, pp. 451 and 596.
Wang, et al., "Respiratory Syncytial virus Fusion Inhibitors. Part 5: Optimization of Benzimidazole Substitution Patterns Towards Derivatives with Improved Activity", Biorganic and Medicinal Chemistry Letters, vol. 17, 2007, pp. 4592-4598.

(Continued)

*Primary Examiner* — Samantha Shterengarts
(74) *Attorney, Agent, or Firm* — Mary A. Appollina

(57) ABSTRACT

A compound satisfying formula I, a prodrug, N-oxide, addition salt, quaternary amine, metal complex, or a stereochemically isomeric form thereof;

formula I

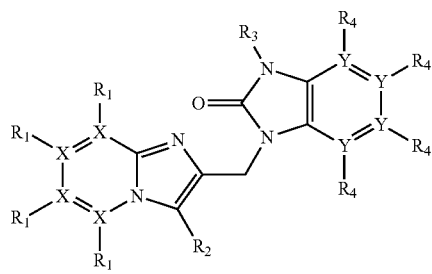

compositions contain these compounds as active ingredient and processes for preparing these compounds and compositions.

17 Claims, No Drawings

(56) References Cited

OTHER PUBLICATIONS

Beaulieu, et al., "Improved Replicon Cellular Activity of Non-Nucleoside Allosteric Inhibitors of HCV NS5B Polymerase: From Benzimidazole to Indole Scaffolds", Biorganic & Medicinal Chemistry letters 16, 2006, pp. 4987-4993.

Goodman, et al, Biotransformation of Drugs:, The Pharmacological Basis of Therapeutics, $8^{th}$ ed., 1992, pp. 13-15.

Giampieri, et al., "Antiviral Activity of Indole Derivatives", Antiviral Research, vol. 83, 2009, pp. 179-185.

Wyde, et al., AWY Dentiviral Research, vol. 38, 1998, pp. 31-42.

Wolff, et al., "Burger's Medicinal Chemistry, $5^{th}$ edition", Part I, pp. 975-977.

Wermuth, "Molecular Variations Based on Isosteric Replacements", Practice of Medicinal Chemistry $3^{rd}$ edition, 2008, pp. 290-342.

Yu, et al., "Respiratory Syncytial Virus Fusion Inhibitors. Part 4: Optimization for Oral Bioavailability" Biorganic & Medicinal Chemistry letters, vol. 17, 2007, pp. 895-901.

Silverman, et al., The Organic of Drug Design and Drug Action, pp. 29-34.

Pearce, et al., "E-Novo: An Automated Workflow for efficient Structure-Based Lead Optimization" J. Chem. Inf. Model, 2009, vol. 49, pp. 1797-1809.

Ito, et al., "A Medium-Term Rat Liver Bioassay for Rapid in Vivo Detection of Carcinogenic Potential of Chemicals" Cancer Science, 94(1) 2003, pp. 3-8.

Database Registry Chemical Abstracts Service, Columbus, Ohio, Assession No. RN 941045-14-3 and RN 931665-23-5.Entered STN: Jul. 4, 2007 and Apr. 22, 2007.

\* cited by examiner

IMIDAZOPYRIDINES AS RESPIRATORY SYNCYTIAL VIRUS ANTIVIRAL AGENTS

CROSS REFERENCE TO RELATED APPLICATIONS

This application is the national stage under 35 U.S.C. 371 of PCT Application No. PCT/EP2011/073017, filed Dec. 16, 2011, which application claims priority from European Patent Application No. EP 10195474.1, filed Dec. 16, 2010 the entire disclosures of which are hereby incorporated by reference in their entirety.

FIELD OF THE INVENTION

The invention concerns imidazopyridines having antiviral activity, in particular, having an inhibitory activity on the replication of the respiratory syncytial virus (RSV). The invention further concerns the preparation of these imidazopyridines, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Reinfection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. The other two drugs, Respi-Gam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

A reference entitles "imidazopyridine and imidazopyrimidine antiviral agents" is WO 01/95910 which, in fact, relates to benzimidazole antiviral agents. Herein compounds are presented to have antiviral activity, yet with $EC_{50}$ values over a wide range of from 0.001 μM to as high as 50 μM (which does not normally represent the desired biological activity). Another reference, relating to substituted 2-methyl-benzimidazole RSV antiviral agents, in the same range of activities is WO 03/053344. Another related background reference on compounds in the same range of activities, is WO 02/26228 regarding benzimidazolone antiviral agents. A reference on structure-activity relations, in respect of RSV inhibition, of 5-substituted benzimidazole compounds is X. A. Wang et al., Bioorganic and Medicinal Chemistry Letters 17 (2007) 4592-4598.

It is desired to provide new drugs that have antiviral activity. Particularly, it would be desired to provide new drugs that have RSV replication inhibitory activity. Further, it would be desired to retrieve compound structures that allow obtaining antiviral biological activities of the order of magnitude in the stronger regions of the prior art (i.e. at the bottom of the above-mentioned range of up to 50 μM), and preferably at a level of about the most active, more preferably of even stronger activity, than the compounds disclosed in the art. A further desire is to find compounds having oral antiviral activity.

SUMMARY OF THE INVENTION

In order to better address one or more of the foregoing desires, the invention, in one aspect, presents antiviral imidazopyridine compounds represented by formula I, a prodrug, N-oxide, addition salt, quaternary amine, metal complex, or a stereochemically isomeric form thereof;

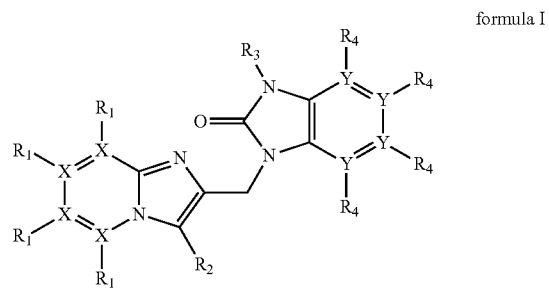

formula I wherein each X independently is C or N;
each Y independently is C or N;
$R_1$ is present when X=C and $R_1$ is selected from the group of H, halogen, $C_1$-$C_6$alkyl, $C_3$-$C_7$cycloalkyl, $C_1$-$C_6$alkoxy, $N(R_5)_2$, $CO(R_6)$, $CH_2NH_2$, $CH_2OH$, CN, C(=NOH)NH$_2$, C(=NOCH$_3$)NH$_2$, C(=NH)NH$_2$, CF$_3$, OCF$_3$, and B(OH)$_2$; B(O—$C_1$-$C_6$alkyl)$_2$;
$R_1$ is absent when X=N
$R_2$ is selected from the group consisting of H, halogen, —(CR$_7$R$_8$)$_n$—R$_9$, C=C—CH$_2$—R$_9$ and CC—R$_9$, and C=C—R$_9$
$R_3$ is selected from the group consisting of H, $C_1$-$C_{10}$alkyl, $C_3$-$C_7$cycloalkyl, $C_2$-$C_{10}$alkenyl, SO$_2$—R$_7$, or a 4 to 6 membered saturated ring containing an oxygen atom;
$R_4$ is present where Y is C and is selected from the group consisting of H, $C_1$-$C_6$alkyl, $C_1$-$C_6$cycloalkyl, $C_1$-$C_6$alkoxy, CO(R$_7$), CF$_3$ and halogen,
$R_4$ is absent when Y=N;
$R_5$ is selected from the group consisting of H, $C_1$-$C_6$alkyl, COOCH$_3$, and CONHSO$_2$CH$_3$;
$R_6$ is selected from the group consisting of OH, O($C_1$-$C_6$alkyl), NH$_2$, NHSO$_2$N($C_1$-$C_6$alkyl)$_2$, NHSO$_2$NHCH$_3$, NHSO$_2$($C_1$-$C_6$alkyl), NHSO$_2$($C_3$-$C_7$cycloalkyl), and N($C_1$-$C_6$-alkyl)$_2$;

$R_7$ and $R_8$ are each independently chosen from H, $C_1$-$C_{10}$alkyl, $C_3$-$C_7$cycloalkyl or $R_2$ and $R_8$ taken together form a 4 to 6 membered aliphatic ring that optionally contains at least one heteroatom selected from the group N, S, O;

$R_9$ is selected from the group consisting of H, $C_1$-$C_6$alkyl, $C_1$-$C_6$ alkoxy, $C_3$-$C_7$cycloalkyl OH, CN, F, $CF_2H$, $CF_3$, $CONR_7R_8$, $COOR_5$, $CON(R_7)SO_2R_8$, $CON(R_7)SO_2N(R_7R_8)$, $NR_7R_8$, $NR_7COOR_8$, $OCOR_7$, $NR_7SO_2R_8$, $SO_2NR_7R_8$, $SO_2R_7$ or a 4 to 6 membered saturated ring containing an oxygen atom;

n is an integer from 2 to 6.

Preferably, $R_7$ and $R_8$ are each independently chosen from H, $C_1$-$C_{10}$alkyl, $C_3$-$C_7$cycloalkyl or $R_7$ and $R_8$ taken together form a 4 to 6 membered aliphatic ring that optionally contains a heteroatom selected from the group N, S, O;

In a preferred embodiment, $R_2$ is selected from the group consisting of H, halogen, —$(CR_7R_8)_n$—$R_9$, C≡C—$CH_2$—$R_9$ and CC—$R_9$ In another aspect, the invention relates to the foregoing compounds for use in the treatment of RSV infections in warm-blooded animals, preferably humans. In yet another aspect, the invention presents a method of treatment of viral RSV infections in a subject in need thereof, comprising administering to said subject an effective amount of a compound as defined above. In still another aspect, the invention resides in the use of a compound as defined above, for the manufacture of a medicament in the treatment of RSV infections.

In a further aspect, the invention relates to a pharmaceutical composition comprising a compound as defined above, and a pharmaceutically acceptable excipient.

In a still further aspect, the invention provides methods for preparing the compounds defined above.

DETAILED DESCRIPTION OF THE INVENTION

The molecules of formula I, in deviation from the prior art, have on one side (the left side in the formula as depicted) an aromatic six-membered ring fused with an imidazole ring, with the six-membered ring including at least one nitrogen atom that is shared by the imidazole ring. In short, this is referred to as a substituted imidazopyridine moiety. It will be appreciated that the term "pyridine" is applicable in the event that all X atoms are C, but the present shorthand term "imidazopyridine" includes all options presented in formula I for the six-membered ring, i.e. irrespective of whether one or more of the X atoms are C or N, e.g. imidazopyrazines.

The invention, in a broad sense, is based on the judicious recognition that these "imidazopyridine" compounds generally possess an interesting RSV inhibitory activity. Moreover, these compounds enable access to anti-RSV activities at the higher regions (lower end of the $EC_{50}$ values) of the range available in the aforementioned references. Particularly, on the basis of these compounds, molecular structures can be uncovered that even outperform the reference compounds in terms of biological activities.

The present invention will further be described with respect to particular embodiments and with reference to certain examples but the invention is not limited thereto but only by the claims. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term 'prodrug' as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8th ed., a McGraw-Hill, Int. Ed. 1992, "Biotransformation of Drugs", p. 13-15) describing prodrugs generally, is hereby incorporated. Prodrugs are characterized by a good aqueous solubility and bioavailability, and are readily metabolized into the active inhibitors in vivo.

As used herein $C_1$-$C_6$alkyl as a group or part of a group defines straight or branched chain saturated hydrocarbon radicals having from 1 to 6 carbon atoms such as methyl, ethyl, propyl, 1-methylethyl, butyl, pentyl, hexyl, 2-methylbutyl and the like.

$C_1$-$C_{10}$alkyl as a group or part of a group defines straight or branched chain saturated hydrocarbon radicals having from 1 to 10 carbon atoms such as the groups defined for $C_1$-$C_6$alkyl and heptyl, octyl, nonyl, 2-methylhexyl, 2-methylheptyl, decyl, 2-methylnonyl, and the like;

The term '$C_2$-$C_{10}$alkenyl' used herein as a group or part of a group is meant to comprise straight or branched chain unsaturated hydrocarbon radicals having at least one double bond, and preferably having one double bond, and from 2 to 10 carbon atoms such as ethenyl, propenyl, buten-1-yl, buten-2-yl, penten-1-yl, penten-2-yl, hexen-1-yl, hexen-2-yl, hexen-3-yl, 2-methylbuten-1-yl, hepten-1-yl, hepten-2-yl, hepten-3-yl, hepten-4-yl, 2-methylhexen-1-yl, octen-1-yl, octen-2-yl, octen-3-yl, octen-4-yl, 2-methylhepten-1-yl, nonen-1-yl, nonen-2-yl, nonen-3-yl, nonen-4-yl, nonen-5-yl, 2-methylocten-1-yl, decen-1-yl, decen-2-yl, decen-3-yl, decen-4-yl, decen-5-yl, 2-methylnonen-1-yl, and the like;

Whenever a $C_2$-$C_{10}$alkenyl group is linked to a heteroatom it preferably is linked via a saturated carbon atom.

$C_1$-$C_6$alkoxy, as a group or part of a group defines an O—$C_1$-$C_6$ alkyl radical, wherein $C_1$-$C_6$ alkyl has, independently, the meaning given above.

$C_3$-$C_7$cycloalkyl is generic to cyclopropyl, cyclobutyl, cyclopentyl, cyclohexyl or cycloheptyl.

The term —$(CR_7R_8)_n$ used herein defines n repetitions of the $CR_7R_8$ subgroup, wherein each of these subgroups is independently defined.

The term halogen is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of general formula (I), their prodrugs, N-oxides, addition salts, quaternary amines, metal complexes and stereochemically isomeric forms.

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i e minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined.

A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates, which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

It will be appreciated that the compounds of the invention, with reference to the aforementioned left- and right-hand parts of formula I, present a wide variety of modification.

Without detracting from the overall scope of the invention, certain embodiments are discussed in more detail below. To facilitate discussion of these embodiments, formula I is presented in an alternative way, with carbon atom numbering and substituent numbering as follows (formula Ia):

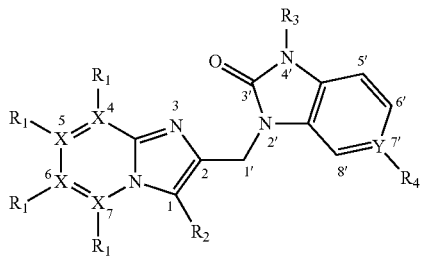

formula Ia

In one embodiment, one of the X numbered 5 or 6 is N. In a preferred embodiment, all X atoms are C.

In one embodiment, all substituents $R_1$ are H. In a preferred embodiment, the substituent on $X^5$ (i.e. $C^5$) is halogen, more preferably Cl or Br.

In a further embodiment, variations are made on $C^1$. Substituent $R_2$ comprises a carbon chain of 2-6 atoms (integer n in the definition of formula I above). Preferably this is 2-4 atoms, more preferably 3-5 atoms. In a more preferred embodiment, the terminus of this substituent, $R_9$, is selected from the group consisting of OH, $OC_1$-$C_6$alkyl, secondary $C_1$-$C_6$alkyl, and more preferably OH, or 2-propyl. "Secondary $C_1$-$C_6$alkyl" is intended to refer to an alkyl moiety that is attached via a non-terminal carbon atom, e.g. 2-propyl, 3-pentyl, and the like. In another preference, $R_2$ is C≡C—C—$R_9$. Herein $R_9$ preferably is $C_1$-$C_6$alkoxy, preferably methoxy, or $C_1$-$C_6$alkyl, preferably branched alkyl.

In a preferred embodiment $R_3$ is $C_3$-$C_7$cycloalkyl, more preferably cyclopropyl.

In a preferred embodiment, and more preferably in conjunction with the other preferred embodiments, one Y is N, and the other Y's are C. In a most preferred embodiment, the one Y that is N, is the Y in para position to N—$R_3$ (i.e. Y at position 7' in formula Ia).

Preferably at most one $R_4$ is selected from the group consisting of H, $C_1$-$C_6$alkyl, $C_1$-$C_6$alkoxy, halogen.

In a preferred embodiment $R_3$ is $C_3$-$C_7$cycloalkyl, more preferably cyclopropyl.

Preferred compounds are the compounds listed in Table 1 below. More preferred are compounds number P1, P2, P3, P4, P5, P6, P7, P8, and P9. Most preferred are compounds P1, P2, P3, and P4.

The compound of formula I may be prepared by the methods described below, using synthetic methods known in the art of organic chemistry, or modifications and derivatisations that are familiar to those of skilled in the art. The starting materials used herein are commercially available or may be prepared by routine methods known in the art such as those methods disclosed in standard reference books. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene and P. G. M. Wuts, Protective Groups in Organic Chemistry, John Wiley & Sons, 1999, which are hereby incorporated by reference.

Compounds of formula I, or their pharmaceutically acceptable salts, can be prepared according to the reaction schemes discussed herein below. Unless otherwise indicated, the substituents in the schemes are defined as above. Isolation and purification of the products is accomplished by standard procedures, which are known to a chemist of ordinary skill.

The following schemes are exemplary of the processes for making compounds of formula I. In the schemes below, the numerals used, including numerals from 1 to XVIII, are used for convenience to designate the formulae in the schemes. The use of numerals from I to XVIII in the schemes below is not intended to imply that the compounds designated by such numerals correspond to the compounds of formulae I to XVIII that are disclosed herein above and that are recited in the appended claims.

Scheme 1: General synthesis of formula I type compounds

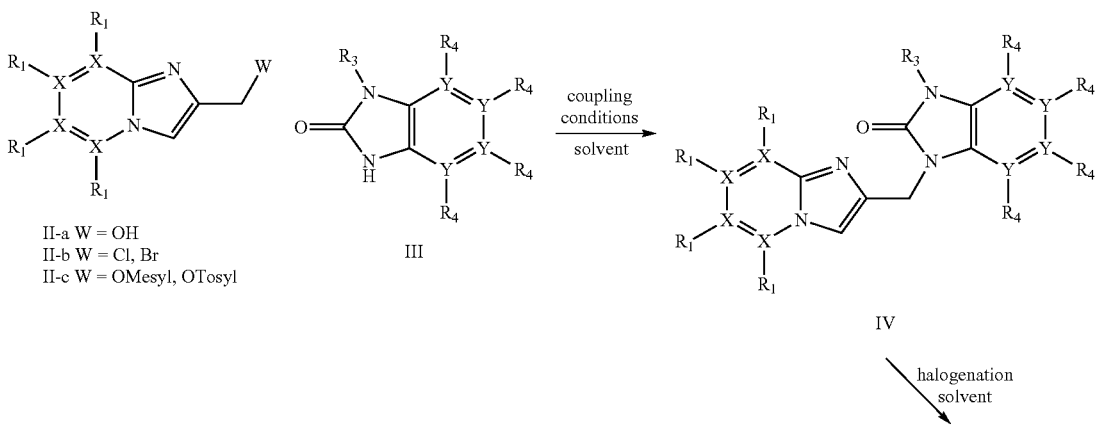

-continued

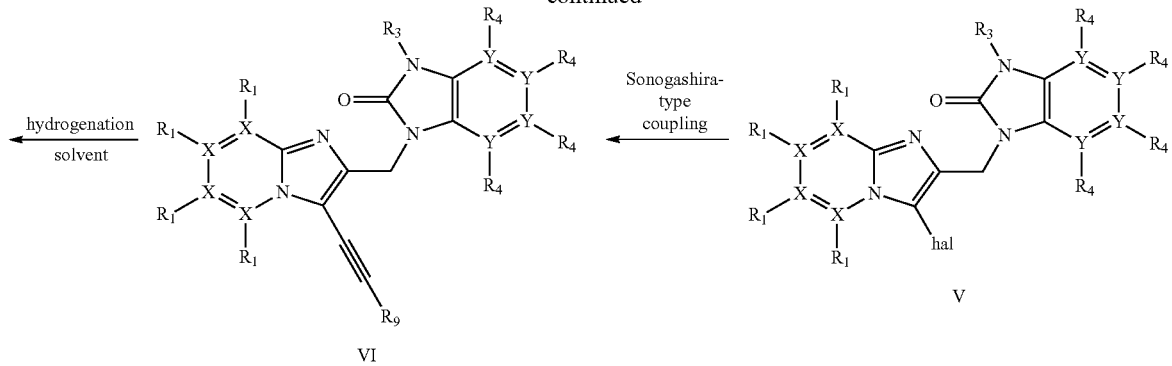

VI     V

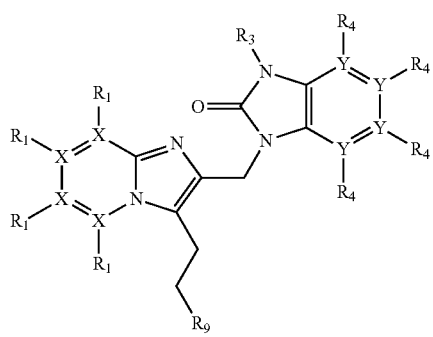

formula I

Scheme 1 illustrates a method for the preparation of compounds of formula I, where $R_1$ to $R_9$, X and Y are defined as above.

A IV type compound can be made by coupling 2-hydroxymethylene imidazopyridine II-a with $N^3$-substituted benzimidazolone III in a known in the art method such as Mitsunobu reaction which use the azadiisopropyldicarboxylate and triphenylphosphine in a suitable solvent such as, but not limiting to, DMF or THF. Alternatively, compounds of formula I may be prepared by displacement of W, which is a halide, II-b, preferably chlorine, or sulfonate, II-c, such as mesylate or tosylate, in the presence of base such as, but not limiting to, sodium hydride, potassium carbonate or cesium carbonate in a suitable solvent such as DMF or THF. Halogenating reagents such as, but not limited to, N-iodosuccinimide can be used to convert a IV type compound to a V type compound and $CH_3CN$ can be a suitable solvent for this reaction. By coupling an alkyn to a V type compound in a known in the art method such as Sonogashira-type coupling reaction, a VI type compound can be generated. Reduction of the triple bond can be done in a catalytic way using hydrogen in the presence of the catalyst such as palladium or platinum, in a suitable solvent such as methanol, or in a stoichiometric way using iron in the presence of ammoniumchloride or tin chloride in the presence of concentrated hydrochloric acid to yield a compound of formula I.

Scheme 2: General synthesis of II-a type compounds

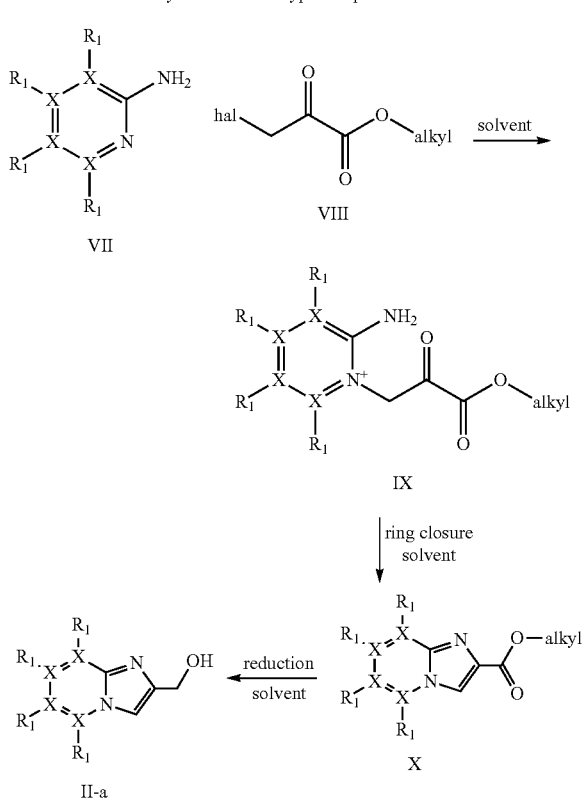

The synthesis of II-a type compounds can generally be prepared as depicted in scheme 2. A IX type compound can be synthesized by coupling a commercially available VII type compound with a commercially available VIII type compound, of which the halogen is preferably bromine, through a base mediated coupling reaction. Possible bases to effect this reaction, but not limiting to, are $K_2CO_3$, $Cs_2CO_3$, triethylamine and sodium hydride. A suitable solvent for this type of base mediated coupling is DME. After an intra molecular ring closure by thermal heating, compounds X can be generated. The conversion of the alkyl ester of compound X to the alcohol II-a was carried out with metal hydride such as lithium aluminum hydride or sodium borohydride in a suitable solvent such as THF or methanol.

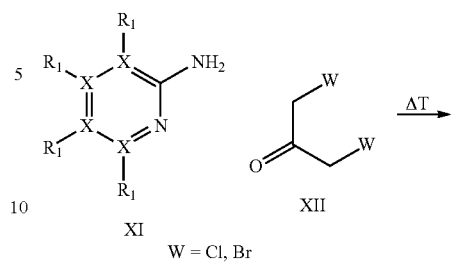

Scheme 3: General synthesis of II-b and II-c type compounds

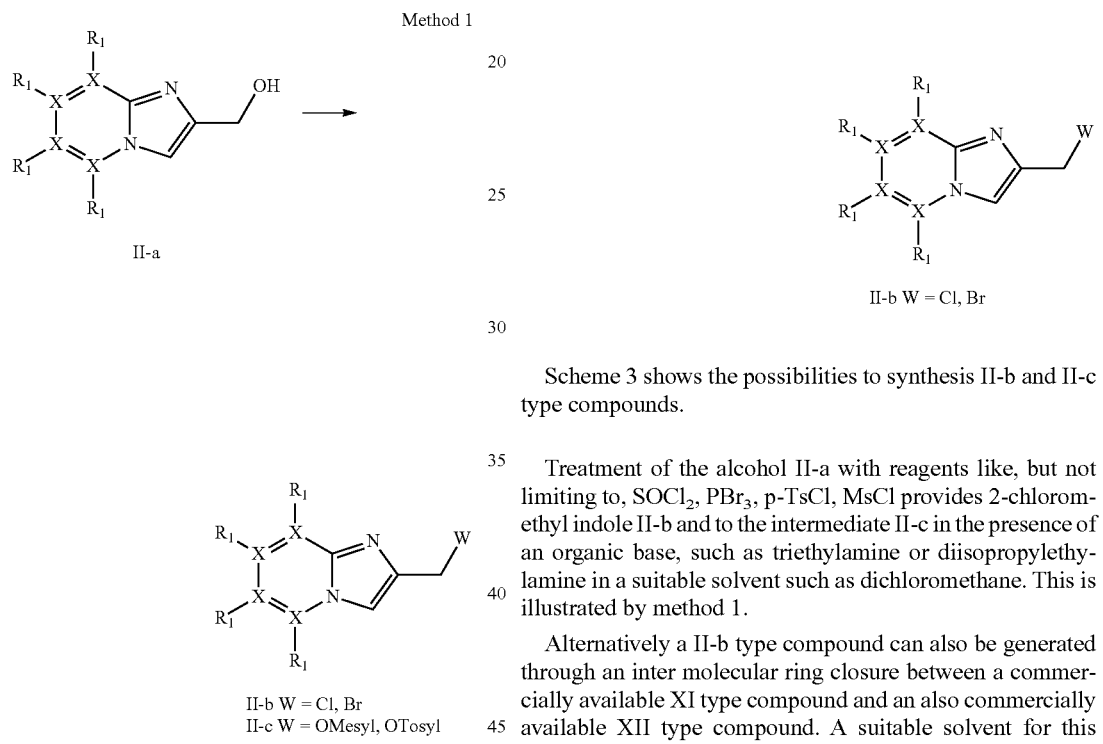

Scheme 3 shows the possibilities to synthesis II-b and II-c type compounds.

Treatment of the alcohol II-a with reagents like, but not limiting to, $SOCl_2$, $PBr_3$, p-TsCl, MsCl provides 2-chloromethyl indole II-b and to the intermediate II-c in the presence of an organic base, such as triethylamine or diisopropylethylamine in a suitable solvent such as dichloromethane. This is illustrated by method 1.

Alternatively a II-b type compound can also be generated through an inter molecular ring closure between a commercially available XI type compound and an also commercially available XII type compound. A suitable solvent for this reaction can be ethanol. This is illustrated by method 2.

Scheme 4: General synthesis of III type compounds

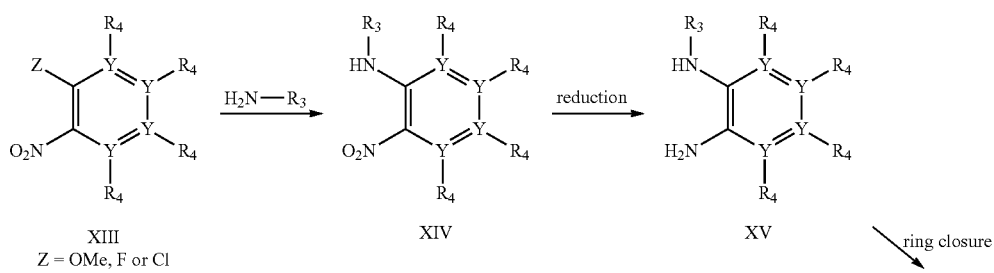

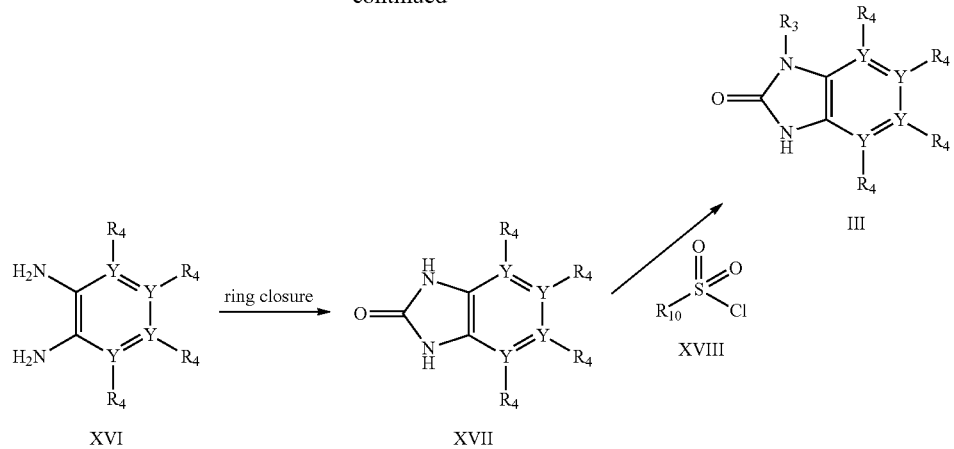

Compounds III can be synthesized using the procedure depicted in scheme 4.

Displacement of Z, which is a halide, preferably fluorine or chlorine, or an alkoxy group, preferably methoxy, of compound XIII with an amine, in a suitable solvent such as THF or DMF, in the presence of an organic base such as triethylamine or diisopropylethylamine, gives compound XIV. Reduction of the nitro group to the amine XV can be done in a catalytic way using hydrogen in the presence of the catalyst such as palladium or platinum, in a suitable solvent such as methanol, or in a stoichiometric way using iron in the presence of ammoniumchloride or tin chloride in the presence of concentrated hydrochloric acid. The cyclization of the resulting diamine XV using CDI, phosgene or triphosgene, in a solvent such as acetonitril or THF, provides compound III.

Alternatively, compounds of type III may be prepared starting from commercially available dianilines XVI which can be cyclized by ring closure with CDI, phosgene or triphosgene yielding intermediates of type XVII. Alkylation or sulfonylation of the urea nitrogen of XVII can be accomplished by a Mitsunobu reaction with commercially available alcohols, or by displacement of the chlorine in the compounds of type XVIII to yield compounds of formula III.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the embodiments of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the embodiments of compounds of formula (I) as specified herein.

Therefore, the compounds of the present invention or any embodiment thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any embodiment thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any embodiment thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any embodiment thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the embodiments of compounds of formula (I), as specified herein.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illlustrated with reference to the following, non-limiting examples.

EXAMPLE 1

A detailed description of the synthesis of representative examples of the invention is given below.

Scheme 5: synthesis of 1-cyclopropyl-1H-imidazo[4,5-c]pyridin-2(3H)-one 5-d

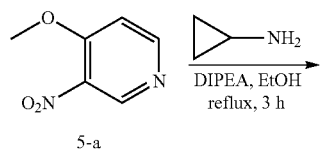

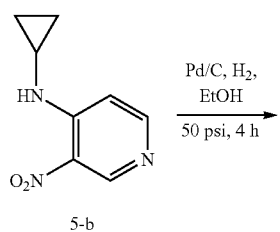

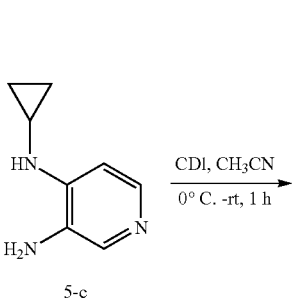

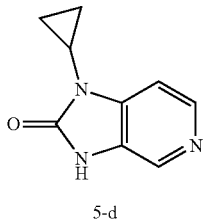

Step 1: Synthesis of N-cyclopropyl-3-nitropyridin-4-amine 5-b

4-Methoxy-3-nitropyridine 5-a (CAS 31872-62-5) (200 g, 1300 mmol), cyclopropylamine (CAS 765-30-0) (185.5 g, 3250 mmol) and DIEA (CAS 7087-68-5) (336 g, 2600 mmol) in dry ethanol (800 mL) were refluxed for 3 hours. The mixture was cooled to 0° C. The solid was collected by filtration. The filter cake was washed with cold ethanol (150 mL). The solid was dried to afford compound 5-b as a white powder (167 g, 72%).

Step 2: Synthesis of $N^4$-cyclopropylpyridine-3,4-diamine 5-c 5-b (167 g, 932 mmol) in ethanol (1400 mL) was hydrogenated (50 Psi) at 20° C. with wet 10% Pd/C (34 g) as a catalyst overnight. After uptake of $H_2$ (3 eq.), the catalyst was filtered off and the filtrate was evaporated. The residue was washed with MTBE to afford compound 5-c as a yellow powder (133 g, 95%).

Step 3: Synthesis of 1-cyclopropyl-1H-imidazo[4,5-c]pyridin-2(3H)-one 5-d

CDI (CAS 530-62-1) (151.8 g, 936 mmol) was added to a solution of 5-c (133 g, 891.4 mmol) in $CH_3CN$ (1800 mL) at 0° C. The reaction was allowed to warm up to room temperature and stirred for 1 hour. The solid was collected by filtration and was washed with $CH_3CN$ (200 mL) to afford compound 5-d as a white powder (101 g, 65%).

Scheme 6: Synthesis of 2-(chloromethyl)imidazo[1,2-a]pyridine 6-c

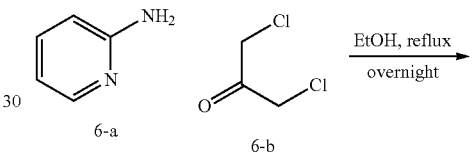

Step 1: Synthesis of 2-(chloromethyl)imidazo[1,2-a]pyridine 6-c

A solution of 1,3-dichloroacetone (CAS 534-07-6) (14.8 g, 116.9 mmol) in absolute ethanol (210 mL) was stirred in a 500 mL flask, charged with a stirring bar, a reflux condenser and an air slot. To the reaction mixture was added 2-aminopyridine 6-a (CAS 504-29-0) (10 g, 106.3 mmol) at room temperature. Then the mixture was heated to reflux overnight. The reaction mixture was concentrated and the residue was taken up in water (300 mL) and basified to pH=9 with saturated $Na_2CO_3$ solution. The solution was extracted with dichloromethane (3×250 mL) and the combined organic layers were washed with brine (300 mL), dried over $MgSO_4$, filtered and concentrated. The product was purified by flash column chromatography, eluting with a gradient of dichloromethane/methanol 0.1% to 2.5%. Concentration of the fractions yielded the product 6-c as a pinkish solid (4.7 g, 27%).

Step 2: Synthesis of 1-cyclopropyl-3-((3-(2-cyclo-propylethyl)imidazo-[1,2-a]pyridin-2-yl)methyl)-1H-imidazo[4,5-c]pyridin-2(3H)-one P3 was extracted with ethyl acetate and the organic layer was dried over Na$_2$SO$_4$, filtered and evaporated. The product was recrystallized in acetonitrile to obtain product 7-a as a pinkish solid (3.19 g, 40%).

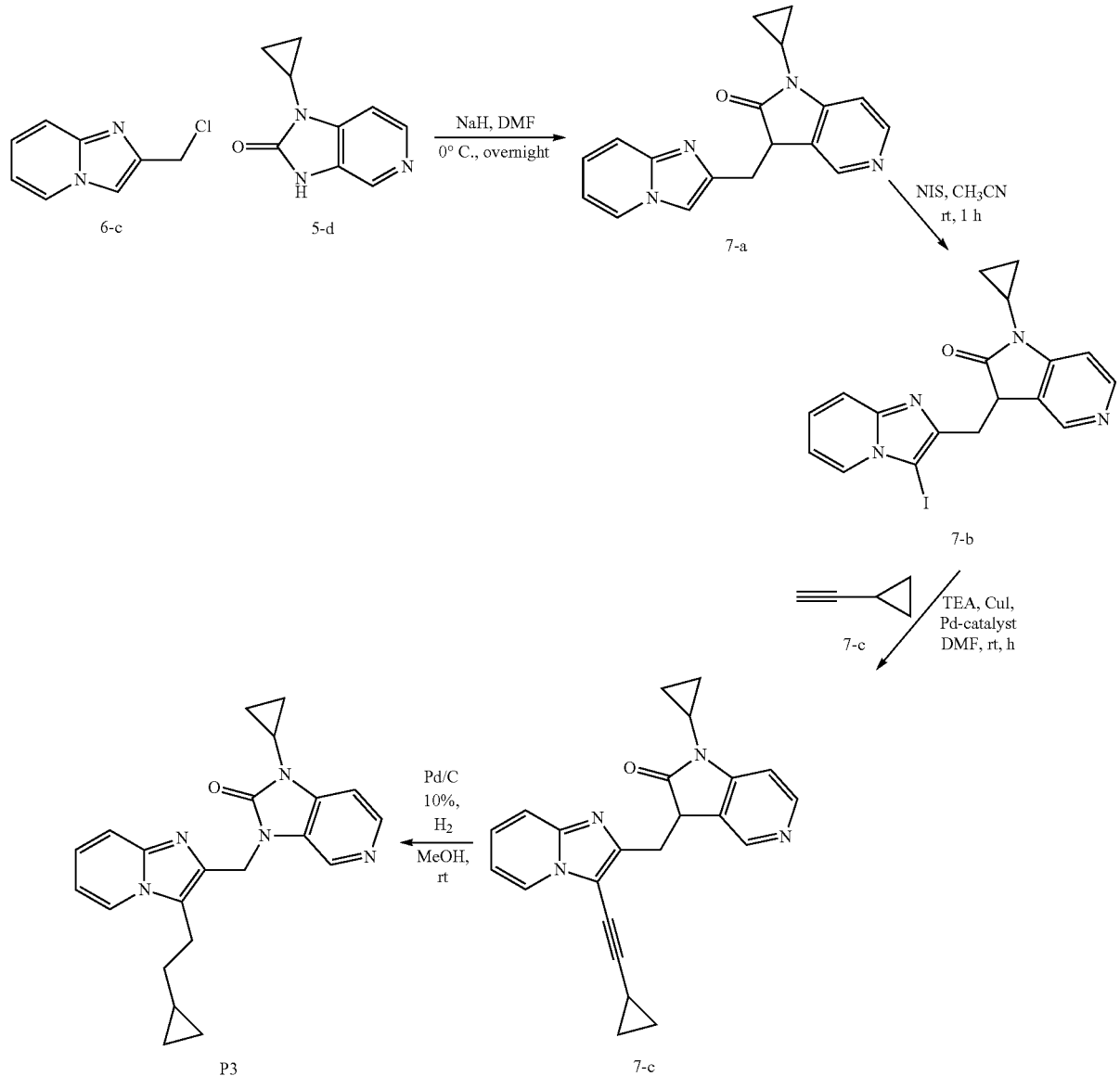

Scheme 7: Synthesis of 1-cyclopropyl-3-((3-(2-cyclopropylethyl)imidazo-[1,2-a]pyridin-2-yl)methyl)-1H-imidazo[4,5-c]pyridin-2(3H)-one P3

Step 1: Synthesis of 1-cyclopropyl-3-(imidazo[1,2-a]pyridin-2-ylmethyl)-1H-imidazo[4,5-c]pyridin-2(3H)-one 7-a To a solution of 5-d (4.5 g, 25.6 mmol) in dry DMF (100 mL) was added at 0° C. a 60% dispersion of NaH (CAS 7646-69-7) (1.1 g, 28.2 mmol). Effervescence was immediate. The reaction mixture was stirred at 0° C. under argon for 30 min. A solution of 6-c (4.7 g, 28.2 mmol) in dry DMF (25 mL) was added to the reaction mixture. The mixture was warmed to room temperature and stirred under argon overnight. To the residue was added water (250 mL). The mixture Step 2: Synthesis of 1-cyclopropyl-3-((3-iodoimi-dazo[1,2-a]pyridin-2-yl)methyl)-1H-imidazo[4,5-c]pyridin-2(3H)-one 7-b To a solution of 7-a (2.5 g, 8.29 mmol) in dry CH$_3$CN (16 mL) was added N-iodosuccinimide (CAS 516-12-1) (2.1 g, 9.11 mmol). The reaction mixture was stirred at room temperature for 1 hour. A precipitate was formed in the reaction. The reaction mixture was cooled to 0° C. to ensure full precipitation. Then the formed solid was filtered off and rinsed with cooled acetonitrile. The obtained solids were collected and thoroughly dried. This gave compound 7-b as an off white solid (3.2 g, 91%).

Step 3: Synthesis of 1-cyclopropyl-3-((3-(cyclopropylethynyl)imidazo[1,2-a]-pyridin-2-yl)methyl)-1H-imidazo[4,5-c]pyridin-2(3H)-one 7-c To a suspension of 7-b (500 mg, 1.16 mmol) in dry DMF (11.6 mL) were added dichlorobis(triphenylphosphine)palladium (CAS 13965-03-2) (244.8 mg, 0.36 mmol), triethylamine (CAS 121-44-8) (0.80 mL, 5.80 mmol)) and copper (I)iodide (CAS 7681-65-4) (66.3 mg, 0.36 mmol). Then cyclopropylacetylene (CAS 6746-94-7) (0.36 mL, 4.17 mmol) was added very slowly and the reaction mixture was stirred at room temperature under nitrogen atmosphere for 2 days. The mixture was concentrated on silicagel and purified by flash column chromatography, eluting with a gradient of dichloromethane/7N NH$_3$ in methanol starting from 1% to 7.5%. The collected fractions were combined and concentrated to yield compound 7-c as yellowish foam (235 mg, 49%).

Step 4: Synthesis of 1-cyclopropyl-3-(3-(2-cyclopropylethyl)imidazo[1,2-a]-pyridin-2-yl)methyl)-1H-imidazo[4,5-c]pyridin-2(3H)-one P3

The catalyst 10% Pd/C (100 mg) and a 4% thiophene solution (0.1 mL) were suspended in methanol (100 mL) under nitrogen atmosphere. Then 7-c (230 mg, 0.56 mmol) was added. The reaction mixture was stirred at 25° C. under hydrogen atmosphere until 2 eq. hydrogen was absorbed. The catalyst was removed by filtration over dicalite. The crude solution was concentrated and purified by flash column chromatography eluting with a gradient of dichloromethane/7N ammonia in methanol (0% to 6%). The collected fractions were evaporated to get product P3 as a white foam (49.9 mg, 23%).

EXAMPLE 2

Synthesis of 3-((7-chloro-3-(4-hydroxybutyl)imidazo[1,2-a]pyridin-2-yl)methyl)-1-cyclopropyl-1H-imidazo[4,5-c]pyridin-2(3H)-one P1

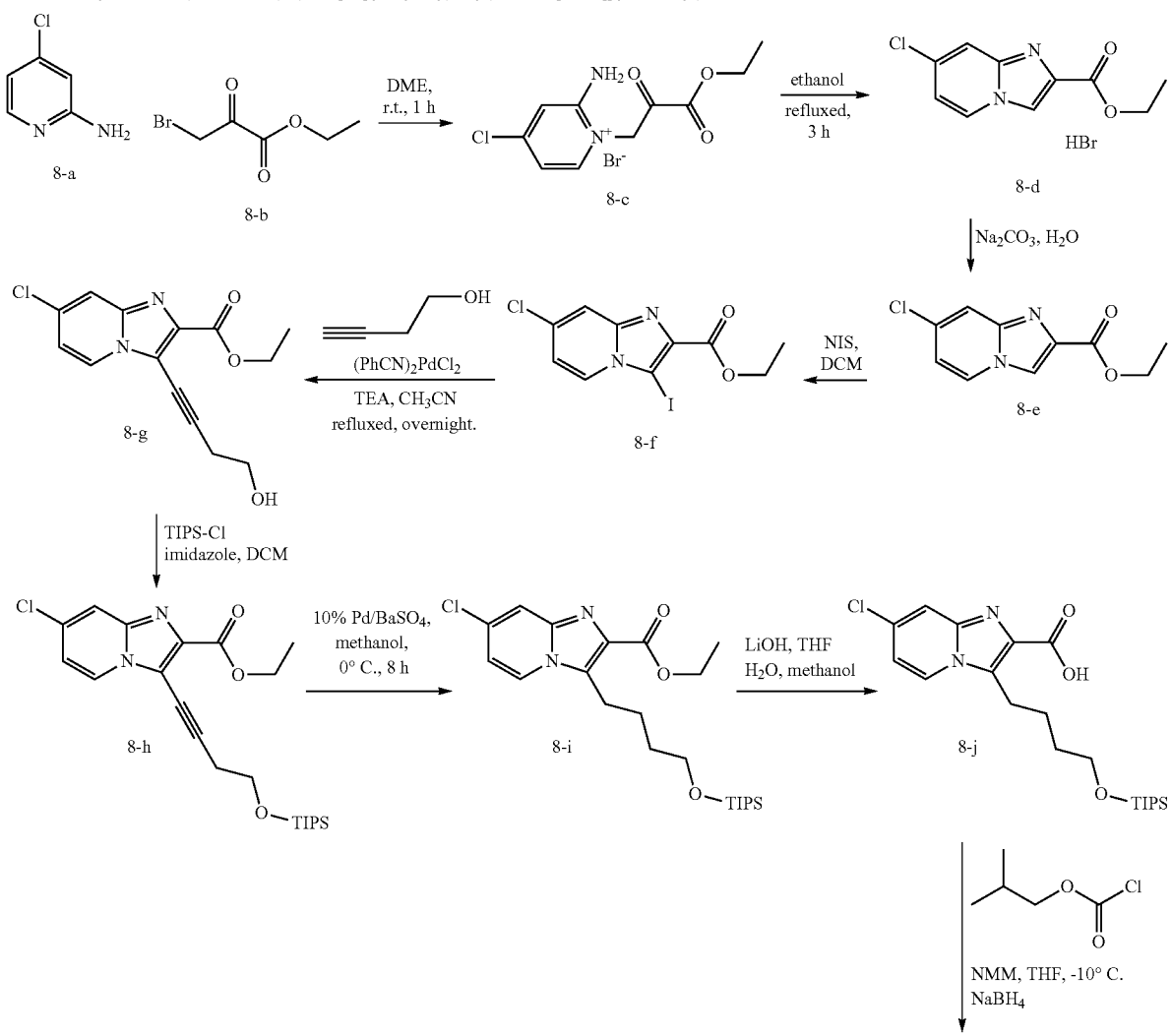

Scheme 8: Synthesis of (7-chloro-3-(4-(triisopropylsilyloxy)butyl)imidazo[1,2-α]pyridin-2-yl)methanol 8-k

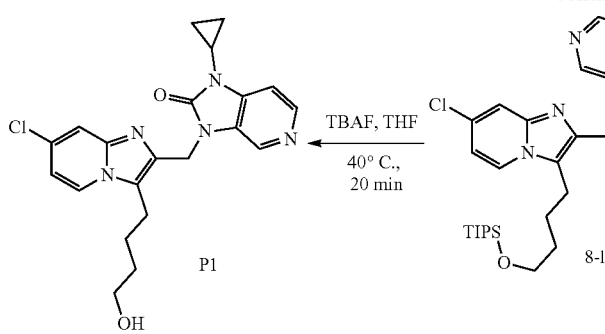
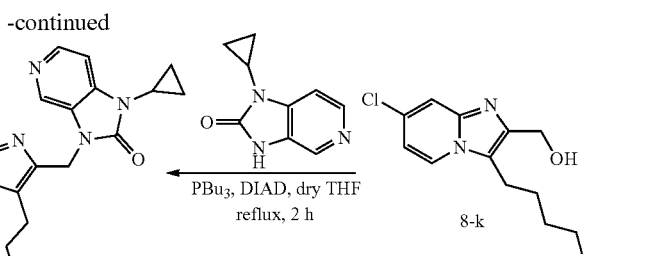

Step 1: Synthesis of 2-amino-4-chloro-1-(3-ethoxy-2,3-dioxopropyl)pyridinium bromide 8-c 4-Chloropyridin-2-amine (CAS 19798-80-2) (47 g, 367 mmol) and ethyl 3-bromo-2-oxopropanoate (CAS 70-23-5) (98 g, 487 mmol) in DME (540 mL) were stirred for 1 hour. The precipitate was filtered and washed with tert-butylmethyl ether to obtain product 8-c as a yellow powder (98 g, 82%).

Step 2: Synthesis of ethyl 7-chloroimidazo[1,2-a]pyridine-2-carboxylate hydrobromide 8-d Intermediate 8-c (98 g, 303 mmol) was dissolved in ethanol (600 mL) and heated at refluxed for 3 hours. The reaction mixture was evaporated and the residue was triturated in ethanol (100 mL) and filtered. The precipitate was washed with tert-butylmethyl ether and dried to afford compound 8-d as a yellow powder (66 g, 71%).

Step 3: Synthesis of ethyl 7-chloroimidazo[1,2-a]pyridine-2-carboxylate 8-e

Intermediate 8-d (51 g, 120 mmol) was dissolved in water (750 mL). $Na_2CO_3$ powder was added carefully until we reach pH=8. The solid was filtered and washed with $H_2O$ (100 mL) and tert-butylmethyl ether. The residue was dried under high vacuum to yield compound 8-e as a white powder (21 g, 78%).

Step 4: Synthesis of ethyl 7-chloro-3-iodoimidazo[1,2-a]pyridine-2-carboxylate 8-f The solid 8-e (10 g, 44.4 mmol) was dissolved in $CH_2Cl_2$ (200 mL). Then NIS (CAS 516-12-1) (20 g, 88.8 mmol) was added at 0° C. and the reaction mixture was stirred at room temperature for 3 hours. The reaction mixture was washed with a saturated $Na_2SO_3$ solution (100 mL) and 10% $K_2CO_3$ solution (100 mL). Then the organic layer was dried over $Na_2SO_4$, filtered and evaporated under vacuum to obtain compound 8-f as a white powder (13.2 g, 85%).

Step 5: Synthesis of ethyl-7-chloro-3-(4-hydroxybut-1-ynyl)imidazo[1,2-a]-pyridine-2-carboxylate 8-g A mixture of intermediate 8-f (8.75 g, 25 mmol), 3-butyn-1-ol (CAS 927-74-2) (10.5 g, 150 mmol), $(PhCN)_2PdCl_2$ (0.95 g, 2.5 mmol) and triethylamine (CAS 121-44-8) (14.5 mL, 150 mmol) was degassed by $N_2$ and refluxed for 3 hours in a $N_2$ atmosphere. The solvent was removed under vacuum and the residue was purified by flash column chromatography eluting with petroleum ether/ethyl acetate (1:3). The solvent was evaporated, the resulting solid was washed with tert-butylmethyl ether and dried under high vacuum to obtain compound 8-g as a white solid (4.75 g, 66%).

Step 6: Synthesis of ethyl 7-chloro-3-(4-(triisopropylsilyloxy)but-1-ynyl)imidazo-[1,2-a]pyridine-2-carboxylate 8-h A mixture of compound 8-g (1.9 g, 6.5 mmol) and imidazole (CAS 288-32-4) (1.37 g, 19.5 mmol) in dry $CH_2Cl_2$ (40 mL) was cooled in an ice water bath. Then TIPS-Cl (CAS 13154-24-0) (1.87 g, 9.8 mmol) was added drop wise at 0° C. The reaction mixture was stirred at room temperature overnight. The mixture was washed with water and brine. The organic layer was dried and evaporated. The residue was purified by flash column chromatography eluting with a gradient starting with pure petrol ether, going to ethyl acetate/petrol ether (1:4). After evaporation of the fractions, product 8-h was obtained as a white solid (2.8 g, 96%).

Step 7: Synthesis of ethyl 7-chloro-3-(4-(triisopropylsilyloxy)butyl)imidazo[1,2-a]-pyridine-2-carboxylate 8-i Compound 8-h (2 g, 4.4 mmol) in methanol was hydrogenated (1 atm) with 5% Pd on $BaSO_4$ (2 g) as a catalyst at 0° C. for 6 hours. After uptake of $H_2$ (2 eq.), the mixture was filtered. The filtrate was concentrated under vacuum and the residue was purified by preparative HPLC. (Column: Grace, Sum, 25×200 mm; gradient eluent, $CH_3CN$/water from 83% to 100%, in the presence of 0.5% of TFA; rate, 25 mL/min) The collected fractions were combined and neutralized by saturated $NaHCO_3$. The organic solvent was removed under vacuum. The remaining aqueous mixture was extracted with ethyl acetate. The organic layer was washed with brine and dried over $Na_2SO_4$. The solvent was removed under vacuum to obtain compound 8-i as a white solid (0.4 g, 20%).

Step 8: Synthesis of 7-chloro-3-(4-(triisopropylsilyloxy)butyl)imidazo[1,2-a]-pyridine-2-carboxylic acid 8-j Intermediate 8-i (0.4 g, 0.88 mmol) and $LiOH.H_2O$ (CAS 1310-66-3) (0.10 g, 2.4 mmol) were suspended in a mixture of THF (4 mL), methanol (4 mL) and water (4 mL). The reaction mixture was stirred at room temperature for 8 hours. Then a 1N HCl solution was added to acidify the mixture to pH=5. The mixture was extracted with ethyl acetate. The organic layer was washed with brine and dried over $Na_2SO_4$.

The solvent was removed under vacuum to yield compound 8-j as a white solid (0.32 g, 86%).

Step 9: Synthesis of (7-chloro-3-(4-(triisopropylsilyloxy)butyl)imidazo[1,2-a]-pyridin-2-yl)methanol 8-k Product 8-j (0.32 g, 0.75 mmol) in dry THF (10 mL) was cooled in an ice water bath. To this cooled mixture NMM (CAS 109-02-4) (0.15 g, 1.5 mmol) and iso-butyl chloroformate (CAS 543-27-1) (0.15 g, 1.1 mmol) were added drop wise. The mixture was stirred at −10° C. for 30 min. Then NaBH$_4$ (CAS 16940-66-2) (0.08 g, 2.2 mmol) was added and stirred again at −10° C. for 30 min. Water was added drop wise to quench the reaction and the remaining mixture was stirred for 1 hour. The mixture was extracted with ethyl acetate. The organic layer was washed with brine and dried over Na$_2$SO$_4$. The solvent was removed under vacuum and the residue was purified by preparative TLC, eluting with petroleum ether/ethyl acetate (1:1), to obtain product 8-k as white foam (0.1 g, 30%).

Step 10&11: Synthesis of 3-((7-chloro-3-(4-hydroxybutyl)imidazo[1,2-a]pyridin-2-yl)methyl)-1-cyclopropyl-1H-imidazo[4,5-c]pyridin-2(3H)-one P1

Intermediate 8-k (0.1 g, 0.24 mmol), intermediate 5-d (0.085 g, 0.48 mmol) and PBu$_3$ (CAS 998-40-3) (0.145 g, 0.72 mmol) were dissolved in dry THF and cooled in an ice methanol bath and degassed by N$_2$. DIAD (CAS 2446-83-5) (0145 g, 0.72 mmol) was added drop wise and the mixture was refluxed under N$_2$ for 2 hours. The solvent was removed under vacuum and the residue was purified by flash column chromatography eluting with ethyl acetate. After evaporation of the fractions we obtain 0.2 g of product 8-1 as a white foam, but which was contaminated with 50% PBu$_3$O. Then intermediate 8-1 and TBAF.3H$_2$O (CAS 429-41-4) (0.15 g, 0.47 mmol) in THF (2 mL) were stirred at 40° C. for 20 min. The solvent was removed under vacuum. The solid residue was washed with water, tert-butylmethyl ether and CH$_3$CN. After drying thoroughly, product P1 was obtained as a white powder (62.0 mg, 62% overall yield).

EXAMPLE 3

Scheme 9: synthesis of 2-(chloromethyl)imidazo[1,2-a]pyrazine 9-a 2-(chloromethyl)imidazo[1,2-a]pyrazine 9-a was synthetized following the protocol described for the synthesis of 2-(chloromethyl)imidazo[1,2-a]pyridine 6-c, using aminopyrazine instead of 2-aminopyridine, and was obtained as a cream solid in 12% yield. m/z = 168(M+H)$^+$.

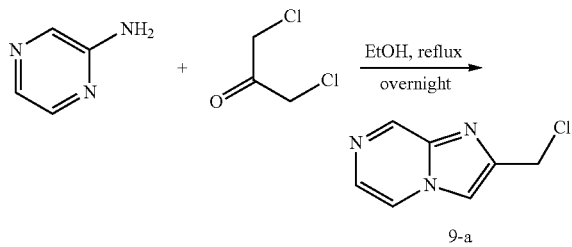

Synthesis of 1-cyclopropyl-3-((3-iodoimidazo[1,2-a]pyrazin-2-yl)methyl)-1H-imidazo[4,5-c]pyridin-2(3H)-one 10-a

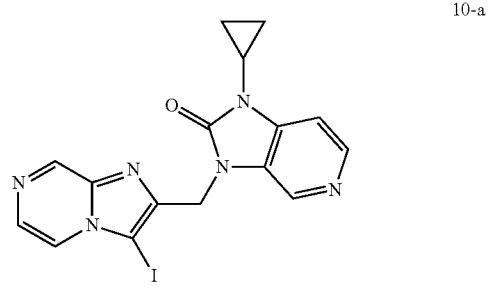 [SMILES: O=c1n(Cc2nc3cnccn3c2I)c2cnccc2n1C1CC1]

10-a 1-cyclopropyl-3-((3-iodoimidazo[1,2-a]pyrazin-2-yl)methyl)-1H-imidazo[4,5-c]pyridin-2(3H)-one 10-a was synthetized following the 2-step procedure reported for the synthesis of 7-b, using 2-(chloromethyl)imidazo[1,2-a]pyrazine 9-a instead of 2-(chloromethyl)imidazo[1,2-c]pyridine 6-c and was obtained as a cream solid. m/z=433 (M+H)$^+$.

EXAMPLE 4

Synthesis of (E)-3-((3-(4-(tert-butyldimethylsilyloxy)but-1-enyl)imidazo[1,2-a]pyrazin-2-yl)methyl)-1-cyclopropyl-1H-imidazo[4,5-c]pyridin-2(3H)-one 11-a

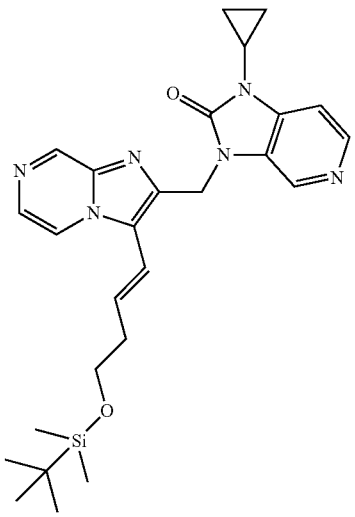 [SMILES: CC(C)(C)[Si](C)(C)OCC/C=C/c1c(Cn2c(=O)n(C3CC3)c3ccncc32)nc2cnccn12]

A suspension of 1-cyclopropyl-3-((3-iodoimidazo[1,2-a]pyrazin-2-yl)methyl)-1H-imidazo[4,5-c]pyridin-2(3H)-one 10-a (500 mg, 1.076 mmole), (E)-tert-butyldimethyl(4-(4,4,5,5-tetramethyl-1,3,2-dioxaborolan-2-yl)but-3-enyloxy)silane (672 mg, 2 eq), sodium carbonate (342 mg, 3 eq), and PdCl$_2$(dppf) (39 mg, 0.05 eq, CAS 72287-26-4) was mixed in DME/water (5 mL/1 mL) and stirred at 100° C. for 2 h. The reaction mixture was then cooled to RT, diluted with 20 mL of DCM, filtrated over dicalite and evaporated. The residue was purified by flash chromatography using a gradient of MeOH 0-5% in DCM and gave the desired product 11-a as a brownish oil in 90% yield. m/z=491 (M+H)⁺.

EXAMPLE 5

Synthesis of 1-cyclopropyl-3-((3-(4-hydroxybutyl)imidazo[1,2-a]pyrazin-2-yl)methyl)-1H-imidazo[4,5-c]pyridin-2(3H)-one P17

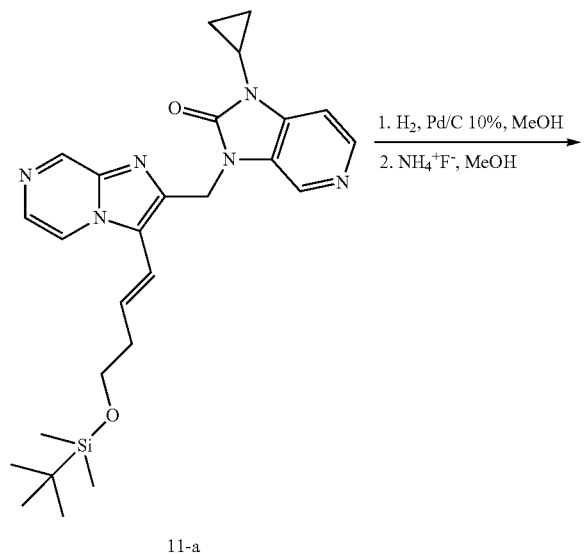

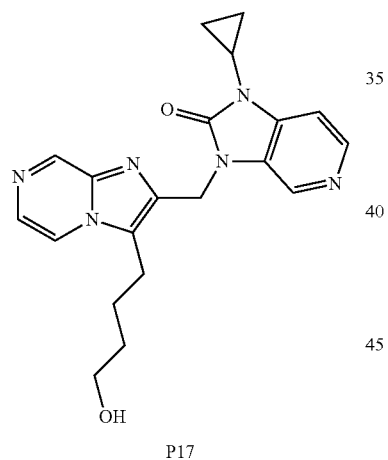

A mixture of (E)-3-((3-(4-(tert-butyldimethylsilyloxy)but-1-enyl)imidazo[1,2-a]pyrazin-2-yl)methyl)-1-cyclopropyl-1H-imidazo[4,5-c]pyridin-2(3H)-one 11-a (480 mg, 0.978 mmole) and Pd/C 10% (52 mg, 0.05 eq) in MeOH (20 mL) was hydrogenated for 2 h. The reaction mixture was then filtered over dicalite and concentrated to dryness. The resulting white solid (480 mg, 84%) was used directly in the next step. It was redissolved in MeOH and ammonium fluoride (39 mg, 1.1 eq) was added. The reaction mixture was then heated at 60° C. overnight. After concentration, the crude was purified by Prep HPLC on (RP Vydac Denali C18-10 μm, 250 g, 5 cm), with the following mobile phase (0.25% NH₄HCO₃ solution in water, CH₃CN), to give the targeted product P17 in 87% yield (320 mg). m/z=491 (M+H)⁺; ¹H NMR (400 MHz, DMSO-d₆) δ ppm 0.82-0.94 (m, 2H), 0.99-1.10 (m, 2H), 1.36-1.46 (m, 2H), 1.46-1.59 (m, 2H), 2.96 (tdd, J=6.96, 6.96, 3.64, 3.51 Hz, 1H), 3.08 (t, J=7.53 Hz, 2 H), 3.34-3.43 (m, 2H), 4.38 (t, J=5.14 Hz, 1H), 5.22 (s, 2H), 7.23 (dd, J=5.27, 0.75 Hz, 1H), 7.88 (d, J=4.52 Hz, 1H), 8.22 (d, J=5.27 Hz, 1H), 8.40 (s, 1H), 8.44 (dd, J=4.64, 1.38 Hz, 1H), 8.97 (d, J=1.51 Hz, 1H).

EXAMPLE 6

Synthesis of 1-cyclopropyl-3-((3-(4-fluorobutyl)imidazo[1,2-a]pyrazin-2-yl)methyl)-1H-imidazo[4,5-c]pyridin-2(3H)-one P18

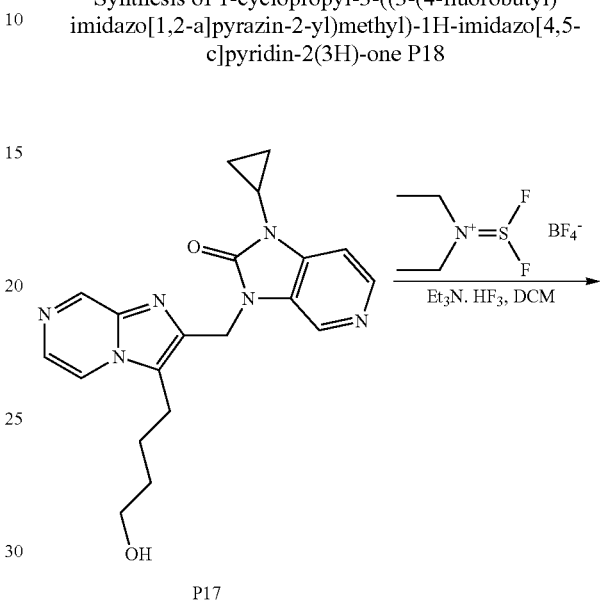

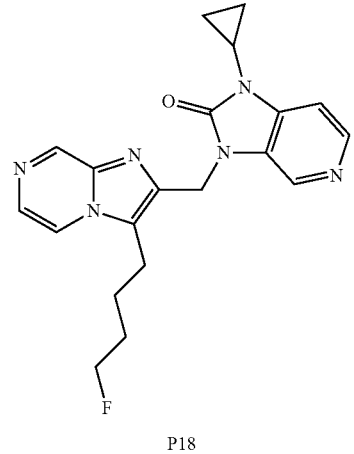

A suspension of diethylaminodifluorosulfonium tetrafluoroborate (453 mg, 1.982 mmole), 1-cyclopropyl-3-((3-(4-hydroxybutyl)imidazo[1,2-a]pyrazin-2-yl)methyl)-1H-imidazo[4,5-c]pyridin-2(3H)-one P17 (500 mg, 1.321 mmole), and triethylamine trihydrofluoride (319 mg, 1.5 eq) in DCM (20 mL) was stirred at RT under N₂ atmosphere for 60 minutes. 100 mL sat NaHCO₃ was then added and the mixture was stirred until gas evolution stopped (10 minutes), then was extracted with 150 mL DCM (2×). Combined organic layers were dried on Na₂SO₄, filtrated and evaporated to dryness. Purification by Prep HPLC on (RP Vydac Denali C18-10 μm, 250 g, 5 cm) with (0.25% NH₄HCO₃ solution in water, MeOH) as mobile phase, afforded the target compound P18 in 20% yield. m/z=381 (M+H)⁺; ¹H NMR (400 MHz, DMSO-d₆) δ ppm 0.82-0.92 (m, 2H), 1.00-1.10 (m, 2H), 1.46-1.80 (m, 4H), 2.95 (tdd, J=6.96, 6.96, 3.64, 3.51 Hz, 1H), 3.12 (t, J=7.53 Hz, 2H), 4.43 (dt, J=47.43, 6.00 Hz, 2H), 5.23 (s, 2H), 7.24 (dd, J=5.27, 0.75 Hz, 1H), 7.89 (d, J=4.52 Hz, 1H), 8.22 (d, J=5.27 Hz, 1H), 8.41 (s, 1H), 8.47 (dd, J=4.77, 1.51 Hz, 1H), 8.98 (d, J=1.51 Hz, 1H).

EXAMPLE 7

Synthesis of (E)-3-((7-chloro-3-(3-morpholino-3-oxoprop-1-enyl)imidazo[1,2-a]pyridin-2-yl)methyl)-1-cyclopropyl-1H-imidazo[4,5-c]pyridin-2(3H)-one P24

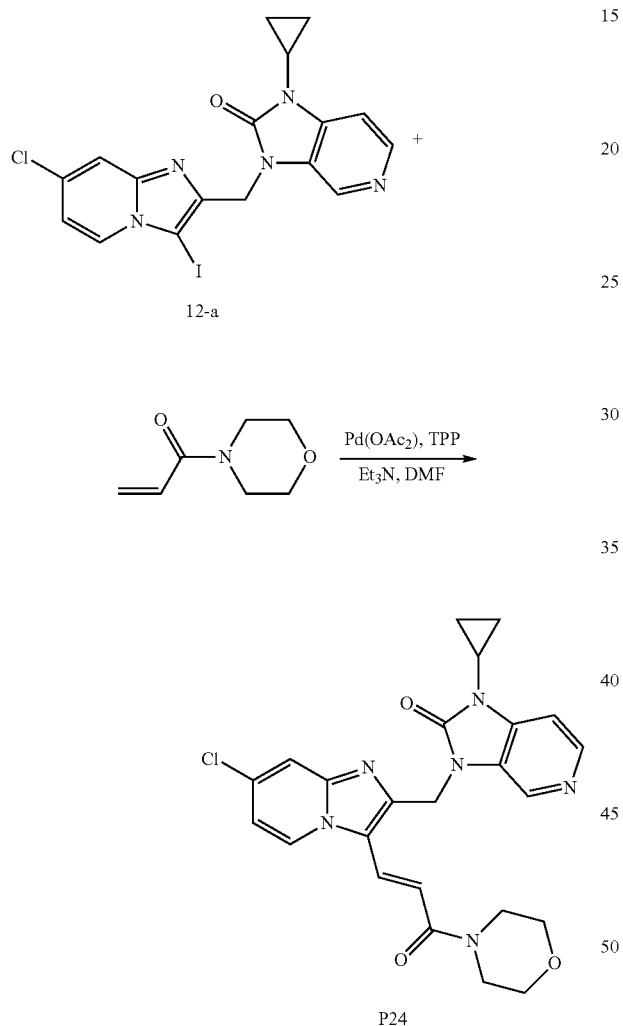

A solution of 3-((7-chloro-3-iodoimidazo[1,2-a]pyridin-2-yl)methyl)-1-cyclopropyl-1H-imidazo[4,5-c]pyridin-2(3H)-one 12-a (prepared following the 3-step synthesis used for 7-b, using 4-chloro-2-aminopyridine instead of 2-aminopyridine in step 1) and Et$_3$N (2.218 mL, 8 eq) in DMF (30 mL) was degassed with nitrogen for fifteen minutes. Then palladium acetate (45 mg, 0.1 eq), triphenylphosphine (173 mg, 0.33 eq) and 1-morpholinoprop-2-en-1-one (2.516 mL, 10 eq) were added and stirring in a closed vessel was allowed at 80° C. during two hours. After cooling the mixture was quenched with ice water. After one hour stirring the precipitate was filtered off and dried in vacuo. The solid was purified over silica with dichloromethane/methanol-NH$_3$ 98/2 as eluent to provide the target compound P24 in 92% yield (884 mg). m/z=479 (M+H)$^+$;

EXAMPLE 8

Synthesis of 3-((7-chloro-3-(3-morpholino-3-oxopropyl)imidazo[1,2-a]pyridin-2-yl)methyl)-1-cyclopropyl-1H-imidazo[4,5-c]pyridin-2(3H)-one P26 and 1-cyclopropyl-3-((3-(3-morpholino-3-oxopropyl)imidazo[1,2-a]pyridin-2-yl)methyl)-1H-imidazo[4,5-c]pyridin-2(3H)-one P27

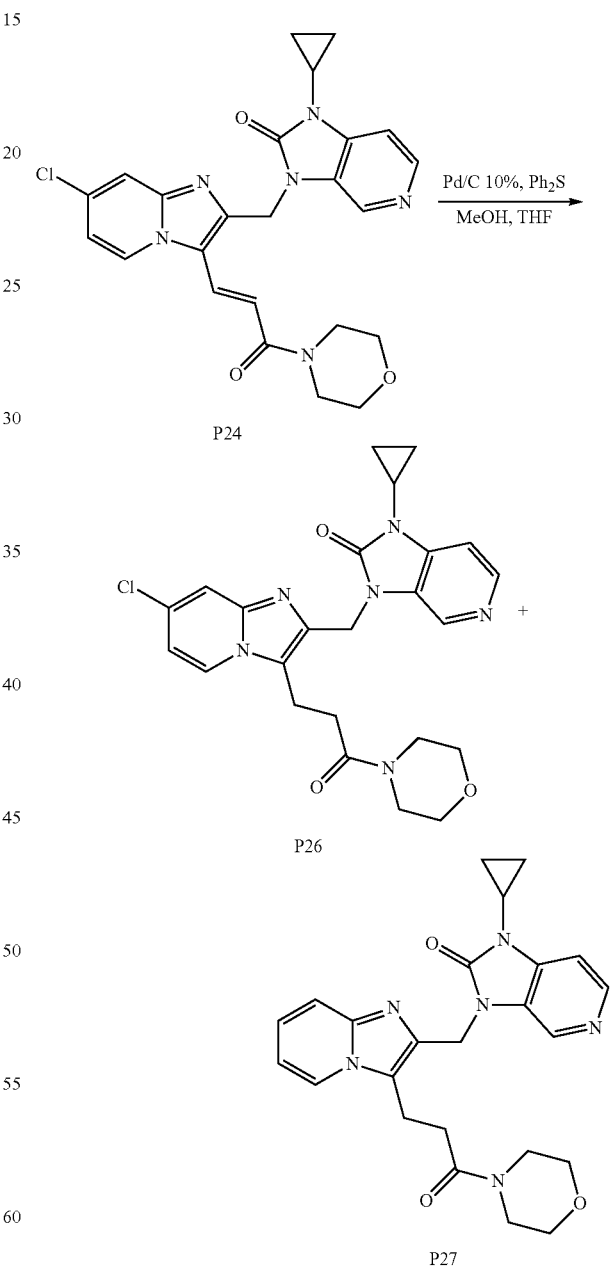

A suspension of (E)-3-((7-chloro-3-(3-morpholino-3-oxoprop-1-enyl)imidazo[1,2-a]pyridin-2-yl)methyl)-1-cyclopropyl-1H-imidazo[4,5-c]pyridin-2(3H)-one P24 (880 mg, 1.837 mmole), Pd/C 10% (195 mg, 0.1 eq) and diphenylsulfide (0.03 mL, 0.1 eq) in MeOH/THF (150 mL, 1/1 mixture) was hydrogenated at room temperature during four hours. The catalyst was then filtered over dicalite under a nitrogen flow and the filtrate was evaporated to dryness. The residue was triturated in acetonitrile/isopropylether 1/1. The precipitate was collected by filtration, dried in vacuo and purified by Prep HPLC on (RP Vydac Denali C18-10 µm, 200 g, 5 cm), with (0.25% $NH_4HCO_3$ solution in water, MeOH+ $CH_3CN$) as mobile phase, to yield 94 mg (10%) of P26 and 241 mg (29%) of P27 as white solids. m/z (P26)=481 $(M+H)^+$; m/z (P27)=447 $(M+H)^+$.

EXAMPLE 9

Characterization of compounds, and test for RSV inhibitory activity.

HPLC-MS analysis was done using either one of the following methods:

Method 1:

The HPLC measurement was performed using an Agilent 1100 module comprising a pump, a diode-array detector (DAD) (wavelength used 220 nm), a column heater and a column as specified below. Flow from the column was split to an Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 mL/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 mL were used. Oven temperature was 50° C. (MS polarity: positive)

Method 2:

The HPLC measurement was performed using an Agilent 1100 module comprising a pump, a diode-array detector (DAD) (wavelength used 220 nm), a column heater and a column as specified below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 mL/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 mL were used. Oven temperature was 50° C. (MS polarity: positive)

Method 3:

Column: XTerra MS C18 2.5 µ, 4.6×50 mm, mobile phase A: 10 mM $NH_4OOCH$+0.1% HCOOH in water, mobile phase B: methanol operating at a column temperature of 50° C. using a flow rate of 1.5 mL/min. Gradient conditions: t=0 min: 65% A, 35% B; t=3.5 min, 5% A, 95% B; t=5.5 min, 5% A, 95% B; t=5.6 min. 65% A, 35% B; t=7 min, 65% A, 35% B.

Method 4:

Column: SunFire C18 3.5 µ 4.6×100 mm, mobile phase A: 10 mM $NH_4OOCH$+0.1% HCOOH in water, mobile phase B: methanol operating at a column temperature of 50° C. using a flow rate of 1.5 mL/min. Gradient conditions: t=0 min. 65% A, 35% B;

t=7 min, 5% A, 95% B; t=9.6 min, 5% A, 95% B; t=9.8 min. 65% A, 35% B; t=12 min, 65% A, 35% B.

NMR spectra were recorded on a Bruker Avance 400 spectrometer, operating at 400 MHz for $^1H$. Chemical shifts are given in ppm and a J value in Hz. Multiplicity is indicated using the following abbreviations: d for doublet, t for a triplet, m for a multiplet, etc. Thin-layer chromatography (TLC) was performed on 5×10 cm aluminium sheets coated with Silicagel 60 $F_{254}$ (Merck KGaA).

Compounds were tested for RSV inbitory activity. The results are depicted in Table 1 and 2 below, with reference to formula Ia and Ib:

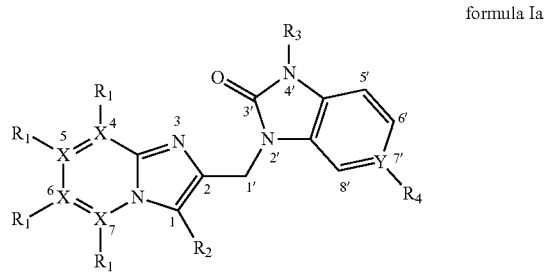

formula Ia

TABLE 1

| | $X_4$—$R_1$ | $X_5$—$R_1$ | $X_6$—$R_1$ | $X_7$—$R_1$ | $R_2$ | $R_3$ | $Y_7$—$R_4$ | $^1$H NMR | LC-MS | WT activity $EC_{50}$ (nM) | Toxicity $CC_{50}$ (nM) |
|---|---|---|---|---|---|---|---|---|---|---|---|
| P1 | C—H | C—Cl | C—H | C—H | 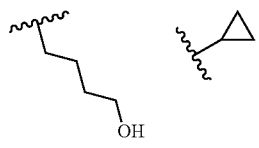 | 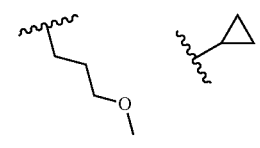 | N | 1H NMR (400 MHz, CHLOROFORM-d) δ ppm 0.94-1.04 (m, 2H) 1.08-1.19 (m, 2H) 1.53-1.65 (m, 4H) 2.58 (br. s., 1H) 2.90 (dt, J = 6.96, 3.42 Hz, 1H) 2.97-3.11 (m, 2H) 3.73 (t, J = 5.40 Hz, 2H) 5.20 (s, 2H) 6.79 (dd, J = 7.28, 2.01 Hz, 1H) 7.12 (d, J = 5.27 Hz, 1H) 7.56 (d, J = 1.51 Hz, 1H) 7.82 (d, J = 7.28 Hz, 1H) 8.30 (d, J = 5.27 Hz, 1H) 8.72 (s, 1H) | 412 (MH)$^+$ | 0.4 | >9840 |
| P2 | C—H | C—Cl | C—H | C—H | 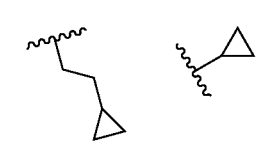 | 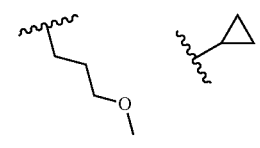 | N | $^1$H NMR (400 MHz, CHLOROFORM-d) δ ppm 0.95-1.04 (m, 2H) 1.09-1.18 (m, 2H) 1.72-1.81 (m, 2H) 2.89 (tdd, J = 6.90, 6.90, 3.76, 3.51 Hz, 1H) 3.11 (t, J =7.40 Hz, 2H) 3.31 (s, 5H) 5.19 (s, 2H) 6.78 (dd, J = 7.40, 2.13 Hz, 1H) 7.09 (d, J = 5.27 Hz, 1H) 7.54 (dd, J = 2.01, 0.50 Hz, 1H) 7.91 (d, J = 7.28 Hz, 1H) 8.29 (d, J = 5.27 Hz, 1H) 8.57(s, 1H) | 412 (MH$^+$) | 3.80 | >9836.03 |
| P3 | C—H | C—H | C—H | C—H | | 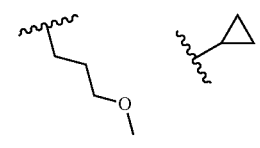 | N | $^1$H NMR (400 MHz, DMSO-d$_6$ δ ppm −0.07--0.01 (m, 2H) 0.26-0.37 (m, 2H) 0.60-0.75 (m, 1H) 0.82-0.93 (m, 2H) 0.99-1.13 (m, 2H) 1.35 (q, J = 7.28 Hz, 2H) 2.94 (tt, J = 6.90, 3.64 Hz, 1H) 3.11 (t, J = 7.53 Hz, 2H) 5.14 (s, 2H) 6.84-6.94 (m, 1H) 7.14-7.27 (m, 2H) 7.49 (d, J = 9.03 Hz, 1H) 8.20 (d, J = 5.27 Hz, 1H) 8.32 (d, J = 6.78 Hz, 1H) 8.43 (s, 1H) | 374 (MH$^+$) | 5.25 | >9836.03 |

TABLE 1-continued

| | X4—R1 | X5—R1 | X6—R1 | X7—R1 | R2 | R3 | Y7—R4 | 1H NMR | LC-MS | WT activity EC50 (nM) | Toxicity CC50 (nM) |
|---|---|---|---|---|---|---|---|---|---|---|---|
| P4 | C—H | C—H | C—H | C—H | isohexyl | cyclopropyl | N | 1H NMR (400 MHz, CHLOROFORM-d) δ ppm 0.79 (d, J = 6.52 Hz, 6H) 0.97-1.05 (m, 2H) 1.10-1.21 (m, 4H) 1.39-1.54 (m, 3H) 2.89 (tt, J = 6.96, 3.58 Hz, 1H) 2.98 (t, J = 7.65 Hz, 2H) 5.23 (s, 2H) 6.79 (td, J = 6.78, 1.25 Hz, 1H) 7.08 (dd, J = 5.27, 0.50 Hz, 1H) 7.13 (ddd, J = 9.16, 6.65, 1.25 Hz, 1H) 7.56 (dt, J = 9.03, 1.00 Hz, 1H) 7.82-7.91 (m, 1H) 8.27 (d, J = 5.27 Hz, 1H) 8.57 (s, 1H) | 390 (MH+) | 7.30 | 83251.11 |
| P5 | C—H | C—H | C—H | C—H | 4-hydroxybutyl | cyclopropyl | N | 1H NMR (400 MHz, DMSO-d6) δ ppm 0.84-0.93 (m, 2H) 1.02-1.10 (m, 2H) 1.36-1.54 (m, 4H) 2.95 (tt, J = 7.02, 3.61 Hz, 1H) 3.04 (t, J = 7.32 Hz, 2H) 3.35-3.43 (m, 2H) 4.37 (t, J = 5.17 Hz, 1H) 5.14 (s, 2H) 6.91 (td, J = 6.83, 1.17 Hz, 1H) 7.16-7.21 (m, 1H) 7.22 (dd, J = 5.17, 0.68 Hz, 1H) 7.51 (dt, J = 9.02, 1.05 Hz, 1H) 8.20 (d, J = 5.07 Hz, 1H) 8.28-8.34 (m, 1H) 8.42 (d, J = 1.00 Hz, 1H) | 378 (MH+) | 21.82 | >100839 |
| P6 | C—H | C—Cl | C—H | C—H | 4-methoxybut-2-ynyl | cyclopropyl | N | 1H NMR (400 MHz, CHLOROFORM-d) δ ppm 0.99-1.09 (m, 2H) 1.14 (m, J = 5.77 Hz, 2H) 2.93 (tdd, J = 7.00, 7.00, 3.64, 3.45 Hz, 1H) 3.39 (s, 3H) 4.36 (s, 2H) 5.30 (s, 2H) 6.90 (dd, J = 7.03, 2.01 Hz, 1H) 7.12 (dd, J = 5.27, 0.50 Hz, 1H) 7.58 (dd, J = 2.01, 0.50 Hz, 1H) 8.11 (dd, J = 7.28, 0.75 Hz, 1H) 8.23 (s, 1H) 8.28 (d, J = 5.27 Hz, 1H) | 408 (MH+) | 169.96 | >9836.03 |

TABLE 1-continued

| | X₄—R₁ | X₅—R₁ | X₆—R₁ | X₇—R₁ | R₂ | R₃ | Y₇—R₄ | ¹H NMR | LC-MS | WT activity EC₅₀ (nM) | Toxicity CC₅₀ (nM) |
|---|---|---|---|---|---|---|---|---|---|---|---|
| P7 | C—H | C—H | C—H | C—H | | | C—H | ¹H NMR (400 MHz, CHLOROFORM-d) δ ppm 0.81 (d, J = 6.44 Hz, 5H) 1.15-1.28 (m, 5H) 1.41-1.51 (m, 3H) 1.54 (d, J = 7.02 Hz, 5H) 3.16 (t, J = 7.71 Hz, 2H) 4.73 (spt, J = 6.99 Hz, 1H) 5.42-5.55 (m, 2H) 7.03-7.13 (m, 2H) 7.16-7.22 (m, 1H) 7.28-7.35 (m, 1H) 7.66-7.76 (m, 1H) 7.96 (d, J = 7.80 Hz, 1H) 8.12 (d, J = 6.83 Hz, 1H) 8.25 (d, J = 9.17 Hz, 1H) | 391 (MH⁺) | 331.00 | 44385.39 |
| P8 | C—H | C—H | C—H | C—H | | | N | ¹H NMR (400 MHz, DMSO-d₆ δ ppm 0.88-0.95 (m, 2H) 1.03-1.10 (m, 2H) 2.08 (s, 2H) 2.98 (tt, J = 7.00, 3.54 Hz, 1H) 5.11-5.22 (m, 2H) 7.05 (td, J = 6.83, 1.17 Hz, 1H) 7.25 (dd, J = 5.27, 0.78 Hz, 1H) 7.33 (ddd, J = 9.02, 6.78, 1.17 Hz, 1H) 7.54 (dt, J = 9.02, 1.05 Hz, 1H) 8.21 (d, J = 5.07 Hz, 1H) 8.23 (s, 1H) 8.32 (dt, J = 6.83, 1.07 Hz, 1H) | 431 (MH⁺) | 531.40 | >49180.2 |
| P9 | C—H | C—H | C—H | C—H | | | C—H | ¹H NMR (400 MHz, CHLOROFORM-d) δ ppm 1.56 (d, J = 7.02 Hz, 6H) 4.80 (dt, J = 14.00, 6.95 Hz, 1H) 5.28 (s, 2H) 6.89 (t, J = 6.83 Hz, 1H) 6.94-6.99 (m, 1H) 7.02 (td, J = 7.61, 1.37 Hz, 1H) 7.09-7.17 (m, 2H) 7.19-7.25 (m, 1H) 7.55 (d, J = 8.98 Hz, 1H) 8.08 (d, J = 6.83 Hz, 1H) | 432 (MH⁺) | 754.68 | >98360.3 |
| P10 | C—H | C—C₄H₈OH | C—H | C—H | | | N | ¹H NMR (400 MHz, DMSO-d₆) δ ppm 0.81-0.94 (m, 2H) 0.98-1.11 (m, 2H) 1.34-1.50 (m, 6H) 1.54-1.66 (m, 2H) 2.60 (t, J = 7.28 Hz, 2H) 2.89-2.97 (m, 1H) 3.00 (t, J = 6.65 Hz, 2H) 3.38-3.64 (m, 4H) 4.39 (dt, J = 7.47, 5.18 Hz, 2H) 5.10 (s, 2H) 6.79 (d, J = 7.03 Hz, 1H) 7.20-7.29 (m, 2H) 8.18-8.25 (m, 2H) 8.42 (s, 1H) | 450 (MH⁺) | >9836.03 | >9836.03 |

TABLE 1-continued

| | $X_4$—$R_1$ | $X_5$—$R_1$ | $X_6$—$R_1$ | $X_7$—$R_1$ | $R_2$ | $R_3$ | $Y_7$—$R_4$ | $^1$H NMR | LC-MS | WT activity $EC_{50}$ (nM) | Toxicity $CC_{50}$ (nM) |
|---|---|---|---|---|---|---|---|---|---|---|---|
| P11 | C—H | C—H | C—H | C—H | | | C—H | $^1$H NMR (400 MHz, CHLOROFORM-d) δ ppm 0.99-1.07 (m, 5H) 1.24-1.32 (m, 1H) 1.51-1.60 (m, 6H) 1.67 (s, 1H) 1.82-1.97 (m, 1H) 2.34-2.41 (m, 2H) 4.80 (spt, J = 6.99 Hz, 1H) 5.26-5.33 (m, 2H) 6.81-6.88 (m, 1H) 6.92-7.04 (m, 2H) 7.07-7.15 (m, 2H) 7.19 (ddd, J = 9.07, 6.83, 1.27 Hz, 1H) 7.53-7.61 (m, 1H) 8.15 (dt, J = 6.83, 1.17 Hz, 1H) | 387 (MH$^+$) | 11282.88 | 34143.65 |
| P12 | C—H | C—H | C—H | C—H | | | C—H | $^1$H NMR (400 MHz, DMSO-d$_6$) δ ppm 1.47 (d, J = 7.02 Hz, 6H) 4.65 (quin, J = 6.98 Hz, 1H) 5.12 (s, 2H) 6.77-6.92 (m, 1H) 6.93-7.09 (m, 2H) 7.12-7.25 (m, 2H) 7.25-7.39 (m, 1H) 7.48 (d, J = 9.17 Hz, 1H) 7.78 (s, 1H) 8.47 (d, J = 6.63 Hz, 1H) | 307 (MH$^+$) | 16124.64 | >98360.3 |
| P13 | C—H | C—H | C—H | C—H | | | N | $^1$H NMR (400 MHz, DMSO-d$_6$) δ ppm 0.82-0.96 (m, 2H) 0.96-1.15 (m, 2H) 2.97 (tt, J = 6.98, 3.56 Hz, 1H) 5.15 (s, 2H) 6.87 (td, J = 6.83, 1.17 Hz, 1H) 7.21 (ddd, J = 9.17, 6.73, 1.27 Hz, 1H) 7.25 (dd, J = 5.27, 0.78 Hz, 1H) 7.48 (dd, J = 9.17, 0.78 Hz, 1H) 7.90 (s, 1H) 8.22 (d, J = 5.27 Hz, 1H) 8.37 (d, J = 0.59 Hz, 1H) 8.48 (dt, J = 6.83, 1.17 Hz, 1H) | 306 (MH$^+$) | 51473.06 | >98360.3 |
| P14 | C—H | N | C—H | C—H | | | N | $^1$H NMR (400 MHz, DMSO-d$_6$) δ ppm 0.88-0.96 (m, 2H) 1.06 (dd, J = 7.12, 2.24 Hz, 2H) 2.98 (t, J = 3.51 Hz, 1H) 5.24 (s, 2H) 7.26 (dd, J = 5.27, 0.78 Hz, 1H) 7.87 (d, J = 4.49 Hz, 1H) 8.07-8.12 (m, 1H) 8.24 (d, J = 5.07 Hz, 1H) 8.36-8.41 (m, 1H) 8.55 (dd, J = 4.49, 1.56 Hz, 1H) 8.99 (d, J = 0.78 Hz, 1H) | 307 (MH$^+$) | >98360.3 | >98360.3 |

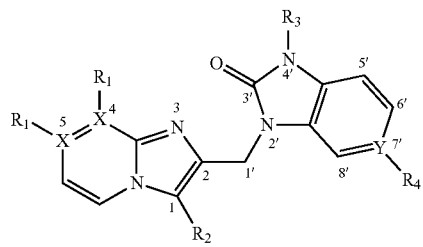

Formula Ib

TABLE 2

| | X₄—R₁ | X₅—R₁ | R₂ | R₃ | Y₇'—R₄ | ¹H NMR | LC-MS | WT activity EC₅₀ (nM) | Toxicity CC₅₀ (nM) |
|---|---|---|---|---|---|---|---|---|---|
| P15 | CH | N | (CH=CH-C(CH₃)₃) | cyclopropyl | N | ¹H NMR (400 MHz, CHLOROFORM-d) δ ppm 0.97-1.06 (m, 2H), 1.10-1.16 (m, 2H), 1.18 (s, 9H), 2.90 (spt, J = 3.60 Hz, 1H), 5.33 (s, 2H), 6.32 (d, J = 17.07 Hz, 1H), 6.46 (d, J = 17.07 Hz, 1 H), 7.11 (dd, J = 5.27, 0.50 Hz, 1H), 7.89 (d, J = 4.77 Hz, 1H), 8.02 (dd, J = 4.77, 1.51 Hz, 1H), 8.28 (d, J = 5.52 Hz, 1H), 8.33 (s, 1H), 9.01 (d, J = 1.51 Hz, 1H) | 389 (MH)⁺ | 318 | >314 |
| P16 | CH | N | (CH₂CH₂-C(CH₃)₃) | cyclopropyl | N | ¹H NMR (400 MHz, CHLOROFORM-d) δ ppm 1.01 (s, 11H), 1.10-1.18 (m, 2H), 1.26-1.36 (m, 2H), 2.90 (tdd, J = 6.90, 6.90, 3.76, 3.51 Hz, 1H), 2.94-3.04 (m, 2H), 5.26 (s, 2H), 7.12 (d, J = 5.27 Hz, 1H), 7.76 (dd, J = 4.52, 1.25 Hz, 1H), 7.87 (d, J = 4.77 Hz, 1H), 8.30 (d, J = 5.27 Hz, 1H), 8.53 (s, 1H), 9.01 (d, J = 1.25 Hz, 1H) | 391 | 172 | >361 |
| P17 | CH | N | (CH₂)₄OH | cyclopropyl | N | ¹H NMR (400 MHz, DMSO-d₆) δ ppm 0.82-0.94 (m, 2H), 0.99-1.10 (m, 2H), 1.36-1.46 (m, 2H), 1.46-1.59 (m, 2H), 2.96 (tdd, J = 6.96, 6.96, 3.64, 3.51 Hz, 1H), 3.08 (t, J = 7.53 Hz, 2H), 3.34-3.43 (m, 2H), 4.38 (t, J = 5.14 Hz, 1H), 5.22 (s, 2H), 7.23 (dd, J = 5.27, 0.75 Hz, 1H), 7.88 (d, J = 4.52 Hz, 1H), 8.22 (d, J = 5.27 Hz, 1H), 8.40 (s, 1H), 8.44 (dd, J = 4.64, 1.38 Hz, 1H), 8.97 (d, J = 1.51 Hz, 1H) | 379 | 276 | >361 |
| P18 | CH | N | (CH₂)₄F | cyclopropyl | N | ¹H NMR (400 MHz, DMSO-d₆) δ ppm 0.82-0.92 (m, 2H), 1.00-1.10 (m, 2H), 1.46-1.80 (m, 4H), 2.95 (tdd, J = 6.96, 6.96, 3.64, 3.51 Hz, 1H), 3.12 (t, J = 7.53 Hz, 2H), 4.43 (dt, J = 47.43, 6.00 Hz, 2H), 5.23 (s, 2H), 7.24 (dd, J = 5.27, 0.75 Hz, 1H), 7.89 (d, J = 4.52 Hz, 1H), 8.22 (d, J = 5.27 Hz, 1H), 8.41 (s, 1H), 8.47 (dd, J = 4.77, 1.51 Hz, 1H), 8.98 (d, J = 1.51 Hz, 1H) | 381 | 544 | >183 |

TABLE 2-continued

| | X$_4$—R$_1$ | X$_5$—R$_1$ | R$_2$ | R$_3$ | Y$_7$—R$_4$ | $^1$H NMR | LC-MS | WT activity EC$_{50}$ (nM) | Toxicity CC$_{50}$ (nM) |
|---|---|---|---|---|---|---|---|---|---|
| P19 | CH | C—Cl | *(structure)* | *(cyclopropyl)* | N | | 466 | | |
| P20 | CH | C—Cl | *(structure)* | *(cyclopropyl)* | N | $^1$H NMR (360 MHz, DMSO-d$_6$) δ ppm 0.83-0.95 (m, 2H), 0.99-1.12 (m, 2H), 2.97 (m, J = 7.0, 3.5, 3.5 Hz, 1H), 3.76 (s, 3H), 5.34 (s, 2H), 6.57 (d, J = 16.5 Hz, 1H), 7.15 (dd, J = 7.7, 2.2 Hz, 1H), 7.26 (d, J = 5.1 Hz, 1H), 7.86 (d, J = 2.2 Hz, 1H), 8.05 (d, J = 16.5 Hz, 1H), 8.23 (d, J = 5.1 Hz, 1H), 8.32 (s, 1H), 8.85 (d, J = 7.3 Hz, 1H) | 424 | 2.97 | >33603 |
| P21 | CH | C—Cl | *(structure)* | *(cyclopropyl)* | N | $^1$H NMR (360 MHz, DMSO-d$_6$) δ ppm 0.84-0.96 (m, 2H), 0.99-1.10 (m, 2H), 2.98 (tt, J = 6.9, 3.6 Hz, 1H), 5.35 (s, 2H), 6.33 (d, J = 16.8 Hz, 1H), 7.20-7.28 (m, 2H), 7.88 (d, J = 2.2 Hz, 1H), 8.15 (d, J = 16.8 Hz, 1H), 8.23 (d, J = 5.5 Hz, 1H), 8.33 (s, 1H), 8.84 (d, J = 7.7 Hz, 1H) | 391 | 13.58 | >3682 |
| P22 | CH | C—Cl | *(structure)* | *(cyclopropyl)* | N | $^1$H NMR (360 MHz, DMSO-d$_6$) δ ppm 0.84-0.92 (m, 2H), 1.00-1.10 (m, 2H), 2.92-3.03 (m, 4H), 3.21 (s, 3H), 5.35 (s, 2H), 7.06-7.18 (m, 2H), 7.26 (d, J = 5.5 Hz, 1 H), 7.84 (m, J = 4.4 Hz, 2H), 8.22 (d, J = 5.1 Hz, 1H), 8.31 (s, 1H), 8.71-8.78(m, 1H) | 437 | | |
| P23 | CH | C—Cl | *(structure)* | *(cyclopropyl)* | N | $^1$H NMR (360 MHz, DMSO-d$_6$) δ ppm 0.82-0.92 (m, 2H), 0.98-1.09 (m, 2H), 2.58 (t, J = 7.3 Hz, 2H), 2.83 (s, 3H), 2.80 (s, 3H), 2.94 (tt, J = 7.0, 3.6 Hz, 1H), 3.24 (t, J = 7.1 Hz, 2H), 5.17 (s, 2H), 6.97 (dd, J = 7.5, 2.0 Hz, 1H), 7.22 (d, J = 5.5 Hz, 1H), 7.66 (d, J = 1.8 Hz, 1H), 8.21 (d, J = 5.5 Hz, 1H), 8.33-8.48 (m, 2H) | 439 | 2.61 | >19156 |
| P24 | CH | C—Cl | *(structure)* | *(cyclopropyl)* | N | | 479 | | |
| P25 | CH | CH | *(structure)* | *(cyclopropyl)* | N | $^1$H NMR (360 MHz, DMSO-d$_6$) δ ppm 0.87 (m, J = 2.6 Hz, 2H), 1.04 (m, J = 5.1 Hz, 2H), 2.55 (t, J = 7.5 Hz, 2H), 2.80 (s, 3H), 2.82 (s, 3H), 2.94 (tt, J = 6.9, 3.6 Hz, 1H), 3.25 (t, J = 7.3 Hz, 2H), 5.17 (s, 2H), 6.90 (t, J = 6.8 Hz, 1H), 7.12-7.27 (m, 2H), 7.48 (d, J = 9.1 Hz, 1H), 8.20 (d, J = 5.1 Hz, 1H), 8.35 (d, J = 7.0 Hz, 1H), 8.41 (s, 1H) | 405 | 15.28 | >6541 |

TABLE 2-continued

| | $X_4$—$R_1$ | $X_5$—$R_1$ | $R_2$ | $R_3$ | $Y_7$—$R_4$ | $^1$H NMR | LC-MS | WT activity $EC_{50}$ (nM) | Toxicity $CC_{50}$ (nM) |
|---|---|---|---|---|---|---|---|---|---|
| P26 | CH | C—Cl | 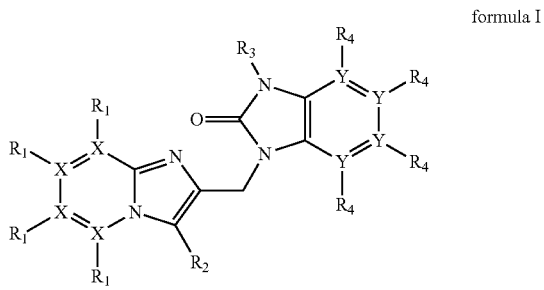 | cyclopropyl | N | $^1$H NMR (360 MHz, DMSO-d$_6$) δ ppm 0.82-0.92 (m, 2H), 0.98-1.10 (m, 2H), 2.61 (t, J = 7.1 Hz, 2H), 2.94 (tt, J = 7.0, 3.5 Hz, 1H), 3.22-3.32 (m, 5H), 3.36-3.51 (m, 5H), 5.16 (s, 2H), 6.98 (dd, J = 7.3, 2.2 Hz, 1H), 7.23 (d, J = 5.1 Hz, 1H), 7.67 (d, J = 2.2 Hz, 1H), 8.21 (d, J = 5.1 Hz, 1H), 8.36-8.44 (m, 2H) | 481 | 2.19 | >22850 |
| P27 | CH | CH | (morpholinyl-butanoyl) | cyclopropyl | N | $^1$H NMR (360 MHz, DMSO-d$_6$) δ ppm 0.88 (m, J = 3.3 Hz, 2H), 1.04 (m, J = 5.1 Hz, 2H), 2.59 (t, J = 7.3 Hz, 2H), 2.94 (tt, J = 7.0, 3.6 Hz, 1H), 3.27 (m, J = 5.5 Hz, 4H), 3.35-3.51 (m, 6H), 5.17 (s, 2H), 6.90 (td, J = 6.8, 1.1 Hz, 1H), 7.20 (m, J = 5.9 Hz, 2H), 7.48 (d, J = 9.1 Hz, 1H), 8.21 (d, J = 5.1 Hz, 1H), 8.34 (d, J = 7.0 Hz, 1H), 8.43 (s, 1H) | 447 | 55.75 | >1793 |

The invention claimed is:

1. A compound satisfying formula I, a prodrug, N-oxide, addition salt, quaternary amine, metal complex, or a stereochemically isomeric form thereof;

formula I wherein each X independently is C or N;
each Y independently is C or N;
$R_1$ is present when X=C and $R_1$ is selected from the group of H, halogen, $C_1$-$C_6$alkyl, $C_3$-$C_7$cycloalkyl, $C_1$-$C_6$alkoxy, $N(R_5)_2$, $CO(R_6)$, $CH_2NH_2$, $CH_2OH$, CN, C(=NOH)NH$_2$, C(=NOCH$_3$)NH$_2$, C(=NH)NH$_2$, CF$_3$, OCF$_3$, and B(OH)$_2$; B (O—$C_1$-$C_6$alkyl)$_2$;
$R_1$ is absent when X=N
$R_2$ is selected from the group consisting of halogen, —(CR$_7$R$_8$)$_n$—R$_9$, C=C—CH$_2$—R$_9$, C≡C—R$_9$, and C=C—R$_9$
$R_3$ is selected from the group consisting of H, $C_1$-$C_{10}$alkyl, $C_3$-$C_7$cycloalkyl, $C_2$-$C_{10}$alkenyl, SO$_2$—R$_7$, or a 4 to 6 membered saturated ring containing an oxygen atom;
$R_4$ is present where Y is C and is selected from the group consisting of H, $C_1$-$C_6$alkyl, $C_1$-$C_6$cycloalkyl, $C_1$-$C_6$alkoxy, CO(R$_7$), CF$_3$ and halogen,
$R_4$ is absent when Y=N;
$R_5$ is selected from the group consisting of H, $C_1$-$C_6$alkyl, COOCH$_3$, and CONHSO$_2$CH$_3$;
$R_6$ is selected from the group consisting of OH, O($C_1$-$C_6$alkyl), NH$_2$, NHSO$_2$N($C_1$-$C_6$alkyl)$_2$, NHSO$_2$NHCH$_3$, NHSO$_2$($C_1$-$C_6$alkyl), NHSO$_2$($C_3$-$C_7$cyclo-alkyl), and N($C_1$-$C_6$-alkyl)$_2$;
$R_7$ and $R_8$ are each independently chosen from H, $C_1$-$C_{10}$alkyl, $C_3$-$C_7$cycloalkyl or $R_7$ and $R_8$ taken together form a 4 to 6 membered aliphatic ring that optionally contains at least one heteroatom selected from the group N, S, O;
$R_9$ is selected from the group consisting of H, $C_1$-$C_6$alkyl, $C_1$-$C_6$ alkoxy, $C_3$-$C_7$cycloalkyl OH, CN, F, CF$_2$H, CF$_3$, CONR$_7$R$_8$, COOR$_7$, CON(R$_7$)SO$_2$R$_8$, CON(R$_7$)SO$_2$N(R$_7$R$_8$), NR$_7$R$_8$, NR$_7$COOR$_8$, OCOR$_7$, NR$_7$SO$_2$R$_8$, SO$_2$NR$_7$R$_8$, SO$_2$R$_7$ or a 4 to 6 membered saturated ring containing an oxygen atom;
n is an integer from 2 to 6.

2. A compound according to claim 1 wherein $R_2$ is selected from the group consisting of halogen, —(CR$_7$R$_8$)$_n$—R$_9$, C=C—CH$_2$—R$_9$ and C≡C—R$_9$.

3. A compound according to claim 1, wherein all X atoms are C.

4. A compound according to claim 1, wherein X—$R_1$ at the para position to the N bridging the imidazole and pyridine ring, is selected from the group consisting of C—H, C—Cl, and C—Br, and all other $R_1$ are H.

5. A compound according to claim 1, wherein $R_7$ and $R_8$ are H and n is 2-4.

6. A compound according to claim 1, wherein $R_9$ is selected from the group consisting of OH, F, CF$_2$H, CF$_3$, and secondary $C_1$-$C_6$ alkyl.

7. A compound according to claim 1, wherein $R_2$ is C=C—CH$_2$—R$_9$ with $R_9$ being selected from the group consisting of $C_1$-$C_6$ alkoxy, $C_1$-$C_6$ straight-chain alkyl, and $C_1$-$C_6$ branched alkyl.

8. A compound according to claim 1, wherein $R_3$ is $C_3$-$C_7$cycloalkyl.

9. A compound according to claim 1, wherein $R_3$ is cyclopropyl.

10. A compound according to claim 1, wherein $R_3$ is isopropyl.

11. A compound according to claim 1, wherein $R_3$ is oxetan-3-yl.

12. A compound according to claim 1, wherein the Y in para position to N—$R_3$ is C and the $R_4$ on that Y is F.

13. A compound according to claim 1, wherein one Y is N, and the other Y's are C, and wherein the one Y that is N is in para position to N—$R_3$.

14. A compound according to claim 1, wherein all $R_4$ are H.

15. A pharmaceutical composition comprising a pharmaceutically acceptable carrier, and as active ingredient a therapeutically effective amount of a compound as claimed in claim 1.

16. A process for preparing a pharmaceutical composition, said process comprising intimately mixing a pharmaceutically acceptable carrier with a therapeutically effective amount of a compound as claimed in claim 1.

17. A method of treating a respiratory syncytial viral (RSV) infection comprising administering to a subject in need thereof an anti-virally effective amount of a compound as claimed in claim 1.

* * * * *